(12) United States Patent
Matsuzawa et al.

(10) Patent No.: US 8,764,634 B2
(45) Date of Patent: Jul. 1, 2014

(54) IMAGING APPARATUS

(71) Applicant: Olympus Medical Systems Corp., Tokyo (JP)

(72) Inventors: Hirohiko Matsuzawa, Hino (JP); Wataru Ono, Hachioji (JP); Hidenori Hashimoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/674,410

(22) Filed: Nov. 12, 2012

(65) Prior Publication Data

US 2013/0096380 A1  Apr. 18, 2013

Related U.S. Application Data

(63) Continuation of application No. PCT/JP2011/073262, filed on Oct. 7, 2011.

(30) Foreign Application Priority Data

Oct. 8, 2010  (JP) .................................. 2010-229002

(51) Int. Cl.
*A61B 1/00* (2006.01)
*A61B 1/04* (2006.01)
*A61B 1/05* (2006.01)
*A61B 1/045* (2006.01)

(52) U.S. Cl.
CPC ......... *A61B 1/00013* (2013.01); *A61B 1/00009* (2013.01); *A61B 1/045* (2013.01); *A61B 1/05* (2013.01)
USPC ............................ 600/109; 600/110; 600/118

(58) Field of Classification Search
CPC ........... A61B 1/00002; A61B 1/00004; A61B 1/00006; A61B 1/00011; A61B 1/00013; A61B 1/00018; A61B 1/00057; A61B 1/00165; A61B 1/05; A61B 1/045; G02B 23/2484; H04N 5/2251
USPC .......... 600/109–110, 118; 382/164, 173, 221, 382/276, 282; 348/65; 396/17
See application file for complete search history.

(56) References Cited

U.S. PATENT DOCUMENTS 5,374,953 A  12/1994 Sasaki et al.
6,154,248 A * 11/2000 Ozawa et al. .................... 348/65

(Continued)

FOREIGN PATENT DOCUMENTS

JP  60-210234 A  10/1985
JP  61-61584 A  3/1986

(Continued)

OTHER PUBLICATIONS

International Search Report PCT/JP2011/073262 dated Nov. 15, 2011.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope system 100 is provided with an optical fiber cable 31 and an electrical cable 32a that transmit pixel information output by a light receiving part 28, an image processor 42 that generates an image based on the pixel information transmitted from the optical fiber cable 31 or the pixel information transmitted from the electrical cable 32a, and a control unit 55 that controls a display unit 71 to display the image generated by the image processor 42, determines whether or not a transmission abnormality is present in the optical fiber cable 31, and selects, as pixel information as a target to be processed by the image processor 42, one of the pixel information transmitted from the optical fiber cable 31 and the pixel information transmitted from the electrical cable 32a depending on a presence of the transmission abnormality in the optical fiber cable 31.

14 Claims, 21 Drawing Sheets

(56) References Cited

U.S. PATENT DOCUMENTS

| | | |
|---|---|---|
| 6,254,531 B1 * | 7/2001 | Higuchi et al. ............... 600/178 |
| 6,597,390 B1 * | 7/2003 | Higuchi ......................... 348/65 |
| 6,734,894 B1 * | 5/2004 | Higuchi et al. ................. 348/69 |
| 6,753,901 B1 * | 6/2004 | Takahashi et al. .............. 348/65 |
| 8,102,434 B2 * | 1/2012 | Yoshida et al. ............ 348/220.1 |
| 2007/0232860 A1 | 10/2007 | Kubo et al. |
| 2011/0216228 A1 * | 9/2011 | Kawamura et al. ........... 348/273 |
| 2012/0016201 A1 * | 1/2012 | Seto et al. ..................... 600/180 |
| 2013/0158352 A1 * | 6/2013 | Imaizumi ...................... 600/111 |
| 2013/0169843 A1 * | 7/2013 | Ono et al. ..................... 348/234 |
| 2013/0201315 A1 * | 8/2013 | Takei et al. ..................... 348/77 |

FOREIGN PATENT DOCUMENTS

| | | |
|---|---|---|
| JP | 4-329923 A | 11/1992 |
| JP | 2006-26133 A | 2/2006 |
| JP | 2007-260066 A | 10/2007 |
| JP | 2009-56240 A | 3/2009 |

* cited by examiner

IMAGING APPARATUS

CROSS-REFERENCE TO RELATED APPLICATIONS

This application is a continuation of International Application No. PCT/JP2011/073262, designating the United States and filed on Oct. 7, 2011 which claims the benefit of priority of the prior Japanese Patent Application No. 2010-229002, filed on Oct. 8, 2010, and the entire contents of the International application and the Japanese Application are incorporated herein by reference.

BACKGROUND OF THE INVENTION

1. Field of the Invention

The present invention relates to an imaging apparatus provided with an imaging unit that is capable of outputting, as pixel information, an electrical signal obtained after a photoelectric conversion from pixels for imaging.

2. Description of the Related Art

Conventionally, an endoscope system has been used in an observation of an inside of organs of a subject in a medical field. In an endoscope system in general, an insertion part having flexibility and an elongated shape is inserted to an inside of a body cavity of a subject such as a patient, a white light is radiated on body tissues in the inside of the body cavity through the inserted insertion part, and a reflection light is received by an imaging unit at a distal end of the insertion part to capture an in-vivo image. The in-vivo image captured in this manner is displayed on a monitor of the endoscope system. A user such as a doctor observes the inside of the body cavity of the subject via the in-vivo image displayed on the monitor of the endoscope system.

In the endoscope system, an imaging element is embedded at the distal end of the insertion part, the imaging element transmits an electrical signal obtained after a photoelectric conversion as an image signal to a signal processor, the signal processor processes the transmitted signal, and thus an image captured by the imaging element is displayed on the monitor to allow an observation of the inside of the subject.

In recent years, a high definition of in-vivo images has been demanded for smoothly making a diagnosis and performing a treatment. In response to the demand, there has been proposed an endoscope system in which an electrical signal is converted into an optical signal at a distal end of an insertion part and the converted optical signal is transmitted to a signal processor by using an optical fiber cable to transmit image signals including volumes of data for supporting and realizing the high definition (see Japanese Patent Application Laid-Open No. 2007-260066).

SUMMARY OF THE INVENTION

An imaging apparatus according to the one aspect of the present invention includes an imaging unit capable of outputting, as pixel information, an electrical signal obtained after a photoelectric conversion from pixels for imaging; a first transmitter that constitutes a first transmission channel that transmits the pixel information output by the imaging unit; a second transmitter that constitutes a second transmission channel that transmits the pixel information output by the imaging unit; a first receiver that receives first pixel information transmitted by the first transmitter; a second receiver that receives second pixel information transmitted by the second transmitter; a selector capable of selecting one of the first pixel information and the second pixel information; a control unit that determines whether or not a transmission abnormality is present in the first transmitter and controls the selector to select one of the first pixel information and the second pixel information depending on a presence of the transmission abnormality in the first transmitter; and an image processor that generates an image based on one of the first pixel information and the second pixel information selected based on the control of the control unit.

The above and other, features, advantages, and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
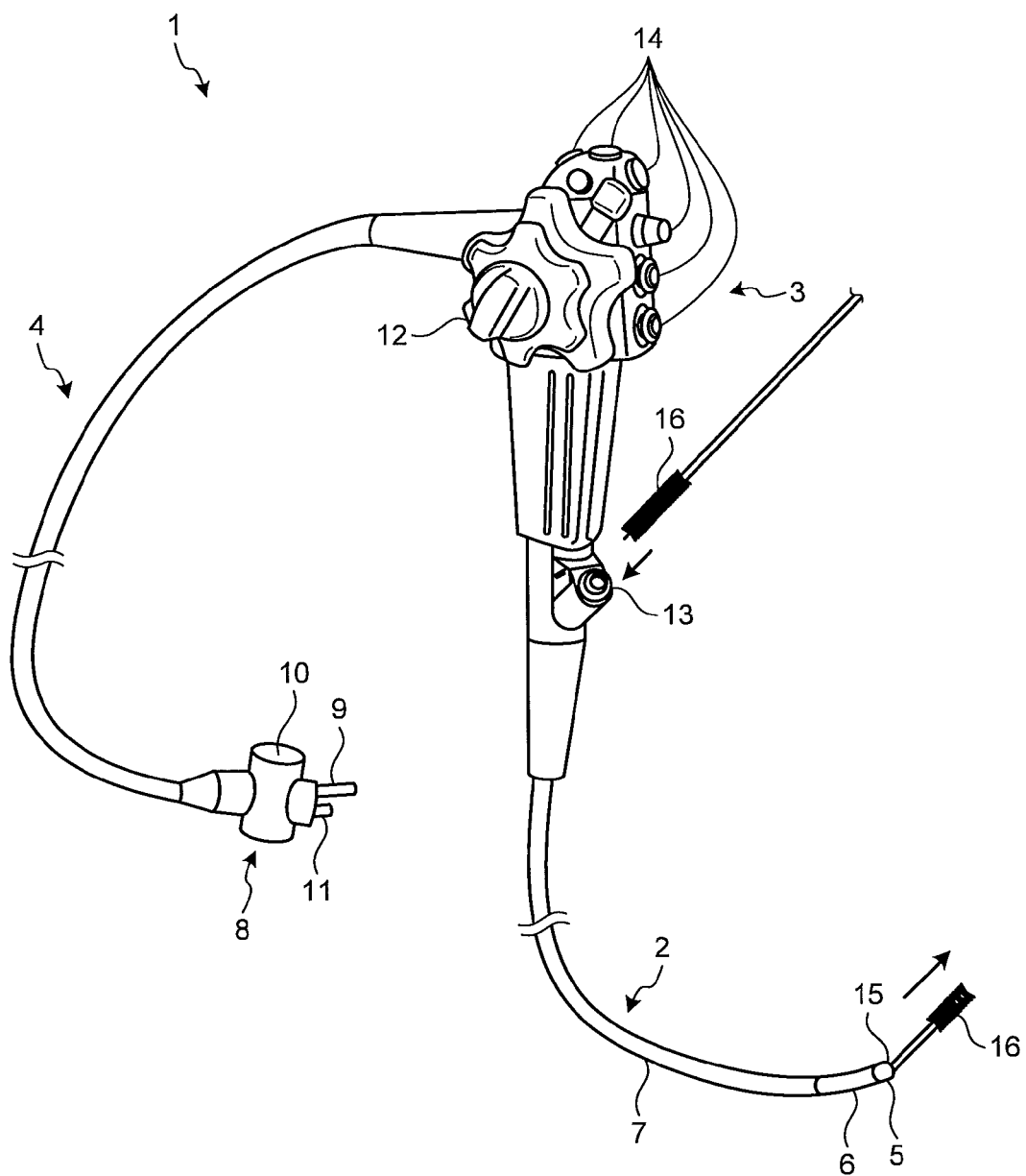
FIG. 1 shows a general structure of an endoscope part according to a first embodiment.

An endoscope system for medical purpose in which an imaging element is provided in a distal end of an insertion part to capture and display an image of an inside of a body cavity of a subject such as a patient will be explained below in exemplary embodiments of the present invention. It should be noted that the present invention is not limited to the embodiments. Throughout the explanation of the drawings, a common part will be provided with a common reference symbol. It should also be noted that the accompanying drawings are merely schematic and a relation between thickness and width and a ratio among parts may be different from the reality. Besides, there may be parts whose dimensional relations and ratios are mutually different in the drawings.

First Embodiment

An endoscope system according to a first embodiment will be explained first. FIG. 1 shows a general structure of an endoscope part in an endoscope system according to a first embodiment. As shown in FIG. 1, an endoscope 1 according to the first embodiment is provided with an elongated insertion part 2, a manipulating part 3 that is provided at a proximal end side of the insertion part 2 and grasped by a manipulator of an endoscope apparatus, and a flexible universal cord 4 that extends from a side of the manipulating portion 3. The universal cord 4 allows embedding a light guiding cable, an electric system cable, and the like.

The insertion part 2 is provided with a distal end part 5 in which a CMOS sensor is embedded as an imaging element, a bend part 6 that is configured to be bendable by a plurality of bending pieces, and a flexible pipe 7 that has a flexibility and an elongated shape and is provided in a proximal end side of the bend part 6.

A connector 8 is provided at an end part of the universal cord 4. In the connector 8, a light guiding connector 9 that is detachably connected to a light source device, an electrical contact part 10 that is connected to a control device for transmitting an electrical signal of a subject image obtained via a photoelectric conversion in the CMOS sensor to the control device for signal processing, an air feeding cap 11 that allows feeding air to a nozzle of the distal end part 5, and the like are provided. Here, the light source device includes a white light source, a specific light source, and the like, and supplies a light from the white light source or the specific light source to the endoscope 1 connected via the light guiding connector 9 as an illumination light. Besides, the control device, which supplies an electric power to the imaging element and to which the electrical signal obtained via the photoelectric conversion from the imaging element is input, processes electric signals obtained through the imaging by the imaging element, controls a display unit to be connected thereto to display an image, and also outputs driving signals for controlling and driving a gain modulation and the like of the imaging element.

In the manipulating part 3, a bend knob 12 that causes the bend part 6 to bend in the vertical direction and the horizontal direction, a treatment tool insertion part 13 through which a treatment tool 16 such as a biopsy forceps and a laser probe is inserted to the inside of the body cavity, a plurality of switches 14 that allow operating a peripheral equipment such as the control device, the light source device, and an air/water/gas feeding unit are provided. The treatment tool 16 inserted through the treatment tool insertion part 13 comes out of an opening 15 at the distal end of the insertion part 2 by way of a treatment tool channel provided inside. In a case where the treatment tool 16 is a biopsy forceps, for example, a biopsy in which diseased tissues are harvested by the biopsy forceps and the like are performed.

Figure 2:
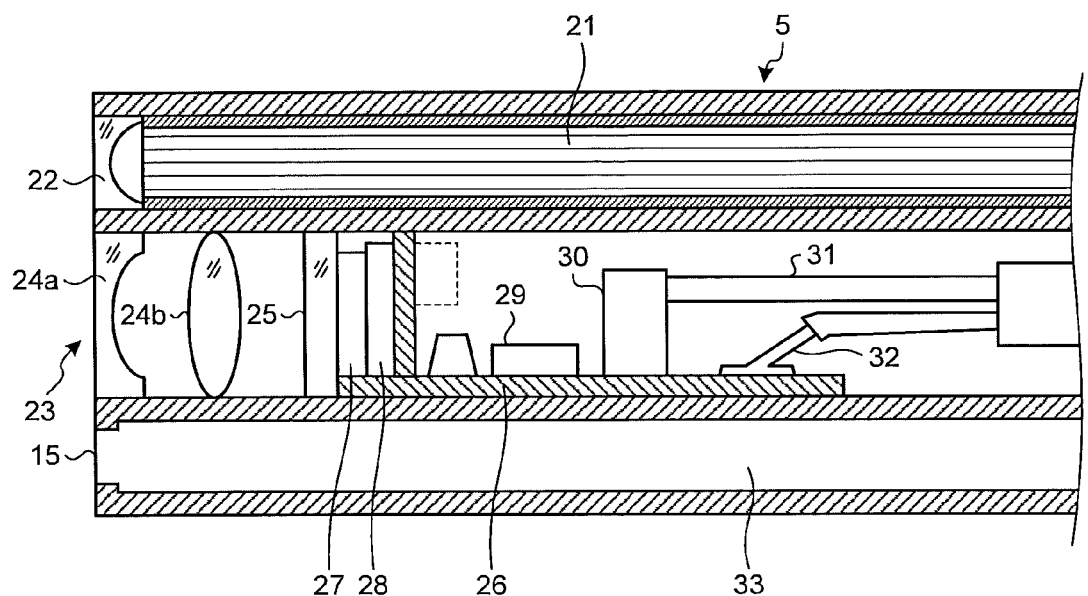
FIG. 2 is a cross sectional view explaining an outline of an inner structure of the distal end part of the endoscope main body shown in FIG. 1.
Figure 3:
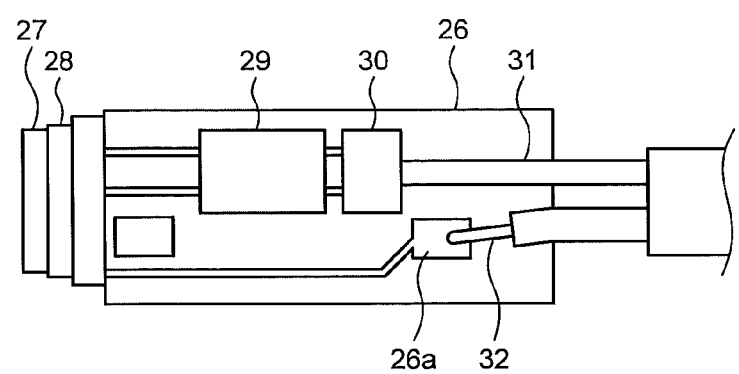
FIG. 3 is a plane view seen from a top of the circuit board shown in FIG. 2.

Next, a structure in the distal end part 5 of the insertion part 2 will be explained. FIG. 2 is a cross sectional view explaining an outline of an inner structure of the distal end part 5 of the endoscope 1 shown in FIG. 1. FIG. 2 shows a case where the distal end part 5 of the endoscope 1 shown in FIG. 1 is cut along an axis and an inside is seen from the cut surface. FIG. 3 is a plane view seen from a top of the circuit board shown in FIG. 2. As shown in FIG. 2, an illumination lens 22, an observation window 23, a treatment tool exposing opening 15 that is communicated with a treatment tool channel 33, and an air/water feeding nozzle (not shown) are provided at the distal end of the insertion part 2 of the endoscope 1.

The white light or the specific light supplied from the light source device is emitted from the illumination lens 22 by way of a light guide 21 configured by a fiberglass bundle and the like. In the observation window 23, a light receiving part 28 including a plurality of imaging pixels arranged two-dimensionally in a matrix state is arranged at a position of the imaging in an optical system constituted by lenses 24a and 24b. The light receiving part 28 receives a light having entered by way of the optical system constituted by the lenses 24a and 24b and captures an image of the inside of the body cavity. A cover glass 25 is provided at a light receiving surface side of the light receiving part 28. Between the cover glass 25 and the light receiving part 28, an on-chip filter 27 on which R, G, and B filters are arranged in accordance with the pixel array of the light receiving part 28 is provided.

As shown in FIGS. 2 and 3, the light receiving part 28 is mounted on a circuit board 26 together with a driver 29 that relays a timing signal to instruct the receiver 28 an imaging timing and supplies an electric power, a conversion circuit that reads out an image signal by the light receiving part 28 and makes a conversion into an electrical signal, and the like.

Figure 4:
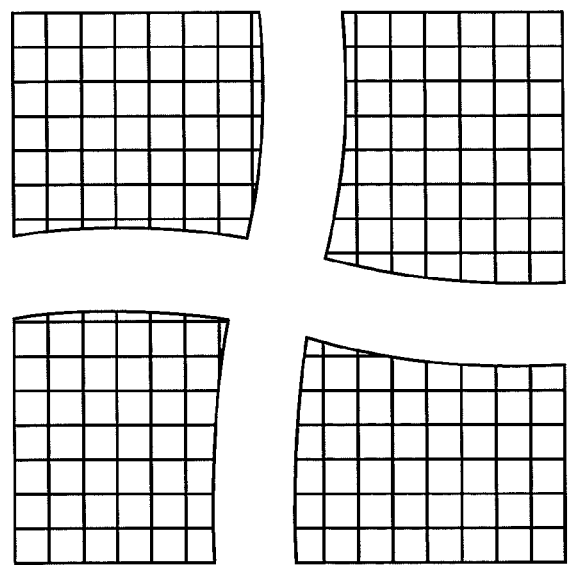
FIG. 4 shows a pixel array of the light receiving part shown in FIG. 2.

In the circuit board 26, an E/O conversion module 30 that converts an electrical signal including the read image signal into an optical signal is mounted. An optical signal converted by the E/O conversion module 30 is transmitted to the control device by an optical fiber cable 31. As shown in FIG. 4, the optical fiber cable 31 transmits an optical signal corresponding to pixel information read out from all the pixels of the light receiving part 28 to the control device.

Figure 5:
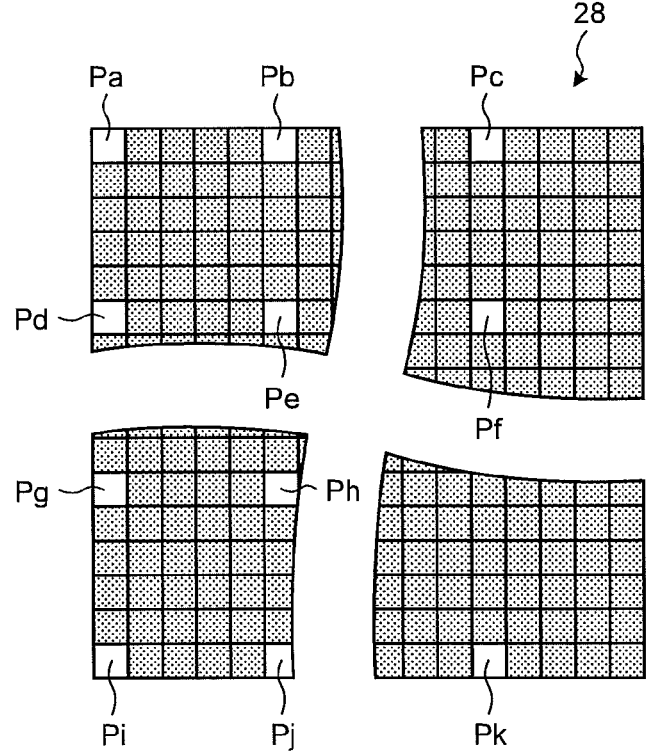
FIG. 5 shows a pixel array of the light receiving part shown in FIG. 2.

A cable assembly 32 is connected to the circuit board 26 via an electrode 26a provided on the circuit board 26. The cable assembly 32 is configured by a plurality of electrical cables to transmit an image signal as an electrical signal output from the light receiving part 28 or to transmit a control signal as an electrical signal from the control device. An electrical cable that transmits an image signal in the cable assembly 32 transmits to the control device an electrical signal corresponding to partial pixel information extracted from information of all of the pixels of the light receiving part 28. The electrical cable that transmits an image signal in the cable assembly 32 transmits information of partial pixels Pa to Pk locating at predetermined intervals as shown in FIG. 5. A volume of signals transmitted by the electrical cable that transmits image signals in the cable assembly 32 is smaller than a volume of signals transmitted by the optical fiber cable 3, the volume by the electrical cable being as small as one several-tenth to one several-hundredth, so that it is possible to make a total volume of signals which can be transmitted by the electrical cable that transmits image signals in the cable assembly 32 smaller than a total volume of signals which can be transmitted by the optical fiber cable 31.

In the first embodiment, two transmitters, i.e., the optical fiber cable 31 and the cable assembly 32, are provided, image signals are simultaneously output from the optical fiber cable 31 and the cable assembly 32, and one of the pixel information transmitted from the optical fiber cable 31 and the pixel information transmitted from the cable assembly 32 is selected as a signal of a pixel as a processing target depending on the presence of abnormality in the optical fiber cable 31 to generate an image.

Figure 6:
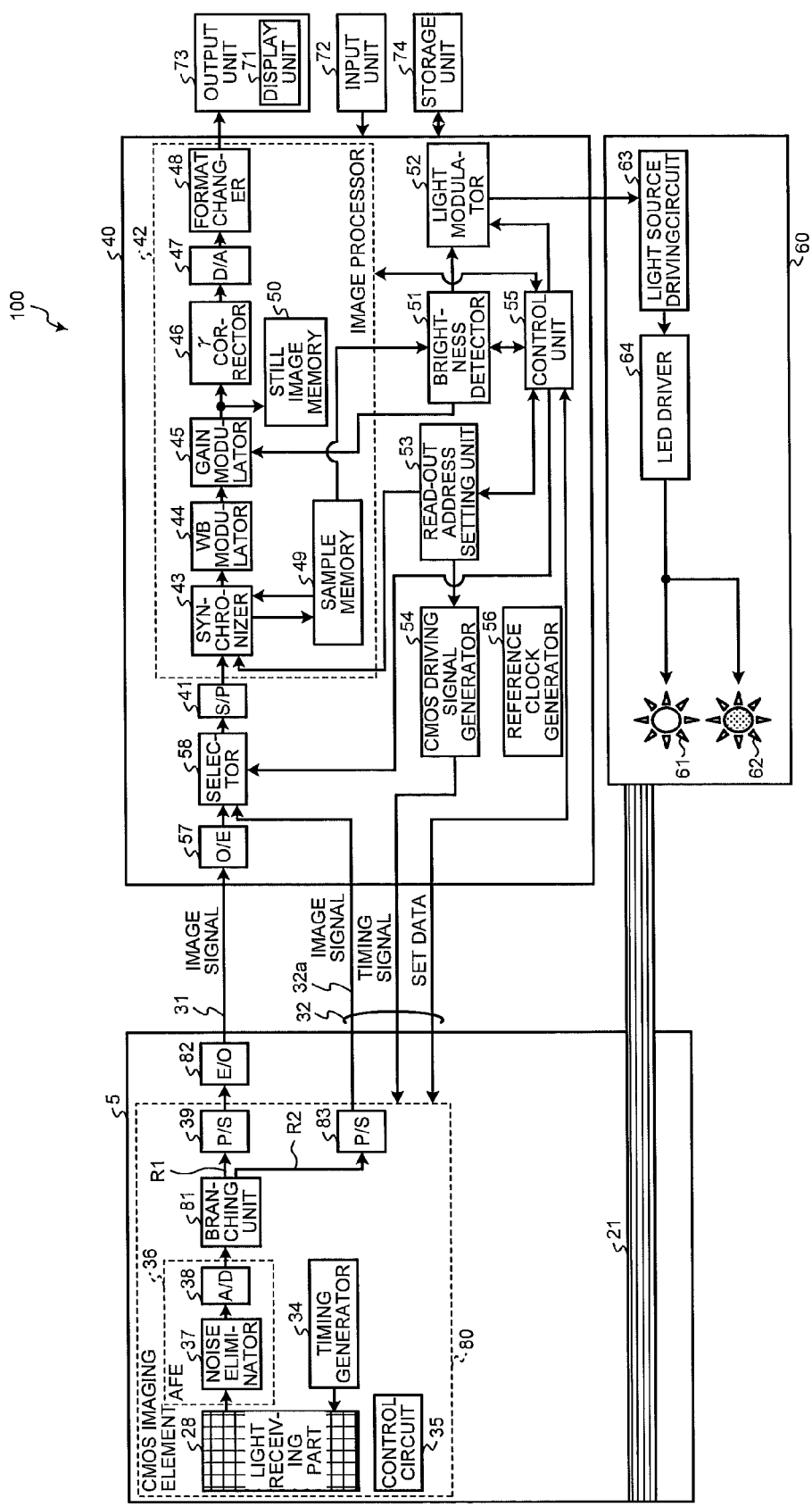
FIG. 6 shows a general structure of an endoscope system according to the first embodiment.

Next, a structure of an endoscope system according to the first embodiment will be explained. FIG. 6 is a block diagram of a structure of an endoscope system according to the first embodiment. As shown in FIG. 6, an endoscope system 100 according to the first embodiment is provided with a control device 40 that is connected to a CMOS imaging element 80 that functions as an imaging unit provided in the distal end part 5 via the optical fiber cable 31 and the cable assembly 32 including a plurality of electrical cables, a light source device 60 that supplies a white light or a specific light, a display unit 71 that displays in-vivo images captured by the CMOS imaging element 80, an output unit 73 that outputs information concerning an observation of an inside of a body, an input unit 72 that inputs instruction information of various kinds necessary for the observation of the inside of the body, and a storage unit 74 that stores in-vivo images and the like.

In the distal end part 5, the CMOS imaging element 80 is provided. The CMOS imaging element 80 is configured by the light receiving part 28, a control circuit 35, a timing generator 34, an analogue front end (AFE) unit 36 constituted by a noise eliminator 37 and an A/D converter 38, and a P/S converter 39 that converts an input digital signal from a parallel form into a serial form.

The light receiving part 28 outputs, as pixel information, electrical signals obtained after a photoelectric conversion from pixels arbitrarily specified as a read-out target among a plurality of pixels for imaging arranged two-dimensionally in a matrix state. The control circuit 35 controls an imaging process of the light receiving part 28, an imaging speed of the light receiving part 28, a read-out process of pixel information from the pixels of the light receiving part 28, and a transmission process of the read-out pixel information in accordance with set data output from the control device 40.

The timing generator 34 is driven in accordance with a timing signal output from the control device 40 to cause an output of an electrical signal obtained after a photoelectric conversion as pixel information from a pixel at a position (address) specified as a read-out target among the plurality of pixels constituting the light receiving part 28. In the first embodiment, all the pixels constituting the light receiving part 28 are specified each as the read-out target and pixel information is read out from all of the pixels of the light receiving part 28.

The noise eliminator 37 eliminates a noise in the pixel information output from a predetermined pixel of the light receiving part 28. The A/D converter 38 converts, from an analogue signal into a digital signal, a signal of the pixel information from which a noise is eliminated and outputs the signal to the P/S converter 39. The timing generator 34 and the AFE unit 36 have a function as a reader in the appended claims.

The pixel information read out by the timing generator 34 and the AFE unit 36 from the light receiving part 28 is output to each of a line R1 connected to the P/S converter 39 at a side of the optical fiber cable 31 and a line R2 connected to a P/S converter 83 at a side of the cable assembly 32 by way of a branching unit 81 that allows branching to the lines R1 and R2.

Figure 7:
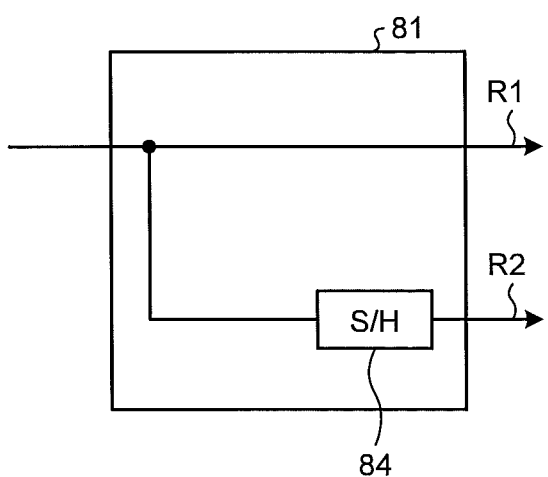
FIG. 7 is an explanatory view of a structure of the branching unit shown in FIG. 6.

As shown in FIG. 7, the branching unit 81 extracts in accordance with a predetermined extraction condition and holds part of the input information on the line R2 branching from the line R1, and is provided with a sample hold (S/H) circuit 84 that performs an output at a predetermined timing. The S/H circuit 84 extracts partial pixel information from the pixel information of all the pixels output from the AFE unit 36 and outputs the extracted information to an electrical cable 32*a* for image signal transmission in the cable assembly 32. For example, the S/H circuit 84 extracts and holds pixel information for the pixels Pa to Pk by not extracting pixel information from a line where the pixels Pa to Pk (see FIG. 5) do not locate among lines in each of which a predetermined number of pixels are arranged and by extracting pixel information at predetermined intervals from lines where the pixels Pa to Pk locate. An electrical signal corresponding to the partial pixel information output from the S/H circuit 84 to the line R2 is converted to an image signal of serial form in the P/S converter 83 and transmitted to the control device 40 via the electrical cable 32*a* of the cable assembly 32.

As shown in FIG. 7, since the input signal is also output to the line R1 without change in the branching unit 81, an electrical signal output to the line R1 deals with pixel information of all the pixels of the light receiving part 28. The electrical signal output to the line R1 is converted to an image signal of serial form in the P/S converter 39, converted from the electrical signal into an optical signal in an E/O converter 82, and then transmitted to the control device 40 via the optical fiber cable 31. Since the optical fiber cable 31 is capable of transmitting signals in large volumes, it is possible to transmit optical signals for pixel information of all the pixels of the light receiving part 28. Therefore, an information volume transmitted by the electrical cable 32*a* becomes smaller than that transmitted by the optical fiber cable 31.

Here, the light receiving part 28 constituting the CMOS imaging element 80, the timing generator 34, the control circuit 35, the AFE unit 36, the branching unit 81, and the P/S converters 39 and 83 are packed onto a single chip, for example.

The control device 40 processes an image signal, controls the display unit 71 to display an in-vivo image, and controls components constituting the endoscope system 100. The control device 40 is provided with an O/E converter 57, a selector 58, an S/P converter 41, an image processor 42, a brightness detector 51, a light modulator 52, a read-out address setting unit 53, a CMOS driving signal generator 54, a control unit 55, and a reference clock generator 56.

The O/E converter 57 converts the optical signal including the pixel information transmitted from the optical fiber cable 31 into an electrical signal.

The selector 58 receives the pixel information transmitted from the optical fiber cable 31 and the pixel information transmitted from the electrical cable 32*a*, also selects one of the received pixel information transmitted from the optical fiber cable 31 and the received pixel information transmitted from the electrical cable 32a, and outputs it to the image processor 42 via the S/P converter 41 under the control by the control unit 55.

The S/P converter 41 converts the image signal as a digital signal output from the selector 58 from a serial form into a parallel form.

The image processor 42 generates an in-vivo image based on the image signal of parallel form output from the S/P converter 41, that is, the pixel information selected by the selector 58 based on the control by the control unit 55, more specifically, based on the pixel information transmitted from the optical fiber cable 31 or the pixel information transmitted from the electrical cable 32a. The image processor 42 generates an in-vivo image that the display unit 71 is made to display based on a pixel address of the light receiving unit 28 read out by the timing generator 34 and the AFE unit 36 with reference to the pixel information read out by the timing generator 34 and the AFE unit 36.

The image processor 42 is provided with a synchronizer 43, a WB modulator 44, a gain modulator 45, a γ corrector 46, a D/A converter 47, a format changer 48, a sample memory 49, and a still image memory 50.

The synchronizer 43 inputs, by associating with a pixel address of the light receiving part 28 read out by the timing generator 34 and the AFE unit 36, an image signal for each of input R, G, and B pixels in a memory (not shown) provided for each pixel, sequentially updates by each input image signal and holds a value in each memory, and synchronizes respective image signals in the three memories as an RGB image signal. Synchronized RGB image signals are sequentially output to the WB modulator 44 and some of the synchronized RGB image signals are also output to the sample memory 49 and held for an image analysis such as brightness detection.

The WB modulator 44 modulates a white balance of the RGB image signal. The gain modulator 45 modulates a gain of the RGB image signal. The γ corrector 46 converts a gradation of the RGB image signal in accordance with the display unit 71.

The D/A converter 47 converts the RGB image signal after the gradation conversion from a digital signal to an analogue signal. The format changer 48 changes to be a format such as a high definition television system and outputs to the display unit 71, the analogue-converted image signal. As a result of this, one in-vivo image is displayed in the display unit 71. A part of RGB image signals whose gain is modulated by the gain modulator 45 is held in the still image memory 50 for a still image display, a magnification image display, or an emphasis image display.

The brightness detector 51 detects a brightness level corresponding to each pixel from the RGB image signals held in the sample memory 49 and stores the detected brightness level in a memory provided in an inside of the brightness detector 51. The brightness detector 51 calculates a gain modulation value and a light irradiation amount based on the detected brightness level. The calculated gain modulation value is output to the gain modulator 45 and the calculated light irradiation amount is output to the light modulator 52. In addition, the result of the detection by the brightness detector 51 is also output to the control unit 55.

The light modulator 52 sets an amount of an electric current to be supplied to each light source and driving conditions of a neutral density filter based on the light irradiation amount output from the brightness detector 51 and outputs a light source synchronization signal including the set conditions to the light source device 60. The light modulator 52 sets a type, an amount, and an emission timing of the light emitted by the light source device 60.

The read-out address setting unit 53 is capable of arbitrarily setting a pixel as a read-out target in the light receiving part 28. Specifically, the read-out address setting unit 53 can arbitrarily set a pixel address of the light receiving part 28 read out by the timing generator 34 and the AFE unit 36. Besides, the read-out address setting unit 53 outputs the address of the pixel as the set read-out target to the synchronizer 43. In the first embodiment, the read-out address setting unit 53 sets all the pixels constituting the light receiving part 28 as the read-out target.

The CMOS driving signal generator 54 generates a driving timing signal that drives the light receiving part 28 and the CMOS sensor peripheral circuit and outputs the generated signal to the timing generator 34 via a predetermined signal line in the cable assembly 32. Here, the timing signal includes a pixel address as a read-out target.

The control unit 55 is configured by a CPU and the like, performs a control of driving components, a control of inputting and outputting information for the components, and an information process for inputting and outputting information of various kinds among the components by reading out various programs stored in a not-shown memory and performing a procedure of each process instructed in the programs. The control device 40 outputs data set for an imaging control to the control circuit 35 of the distal end part 5 via a predetermined signal line of the cable assembly 32. The set data includes an imaging speed of the light receiving part 28, instruction information instructing a speed of reading pixel information from a given pixel of the light receiving part 28, and transmission control information of the read pixel information.

The control unit 55 determines a transmission abnormality of the optical fiber cable 31 based on the presence of the pixel information (image signals) transmitted from the optical fiber cable 31 to the control device 40. The control unit 55 then controls the selector 58 to select, as a pixel signal of a processing target of the image processor 42, one of the pixel information transmitted from the optical fiber cable 31 and the pixel information transmitted from the electrical cable 32a, depending on the presence of the transmission abnormality in the optical fiber cable 31. Specifically, when the transmission abnormality is not present in the optical fiber cable 31, the control unit 55 outputs a control signal of instructing a selection of the pixel information transmitted from the optical fiber cable 31 to the selector 58 to cause the selector 58 to select and output the pixel information transmitted from the optical fiber cable 31. Besides, when the transmission abnormality is present in the optical fiber cable 31, the control unit 55 outputs a control signal of instructing a selection of the pixel information transmitted from the electrical cable 32a to the selector 58 to cause the selector 58 to select and output the pixel information transmitted from the electrical cable 32a. The control unit 55 also performs a display controlling process of making the display unit 71 display the image generated by the image processor 42.

The reference clock generator 56 generates a reference clock signal which serves as a reference in operation of each component of the endoscope system 100 and provides the generated reference clock signal to each component of the endoscope system 100.

The light source device 60 operates under the control of the control unit 55. The light source device 60 is provided with a white light source 61 that radiates a white illumination light configured by an LED and the like, a specific light source 62 that radiates, as a specific light, any one of RGB lights which are different in wavelength band from the white illumination light and whose bands are narrowed by a narrow band-pass filter, a light source driving circuit 63 that controls an amount of an electric current to be supplied to the white light source 61 or the specific light source 62 and a driving of the neutral density filter in accordance with the light source synchronization signal transmitted from the light modulator 52, and an LED driver 64 that supplies a predetermined amount of electric current to the white light source 61 or the specific light source 62 under the control of the light source driving circuit 63. The light radiated from the white light source 61 or the specific light source 62 is supplied to the insertion part 2 via the light guide 21 and emitted outward from the distal end of the distal end part 5.

Figure 8:
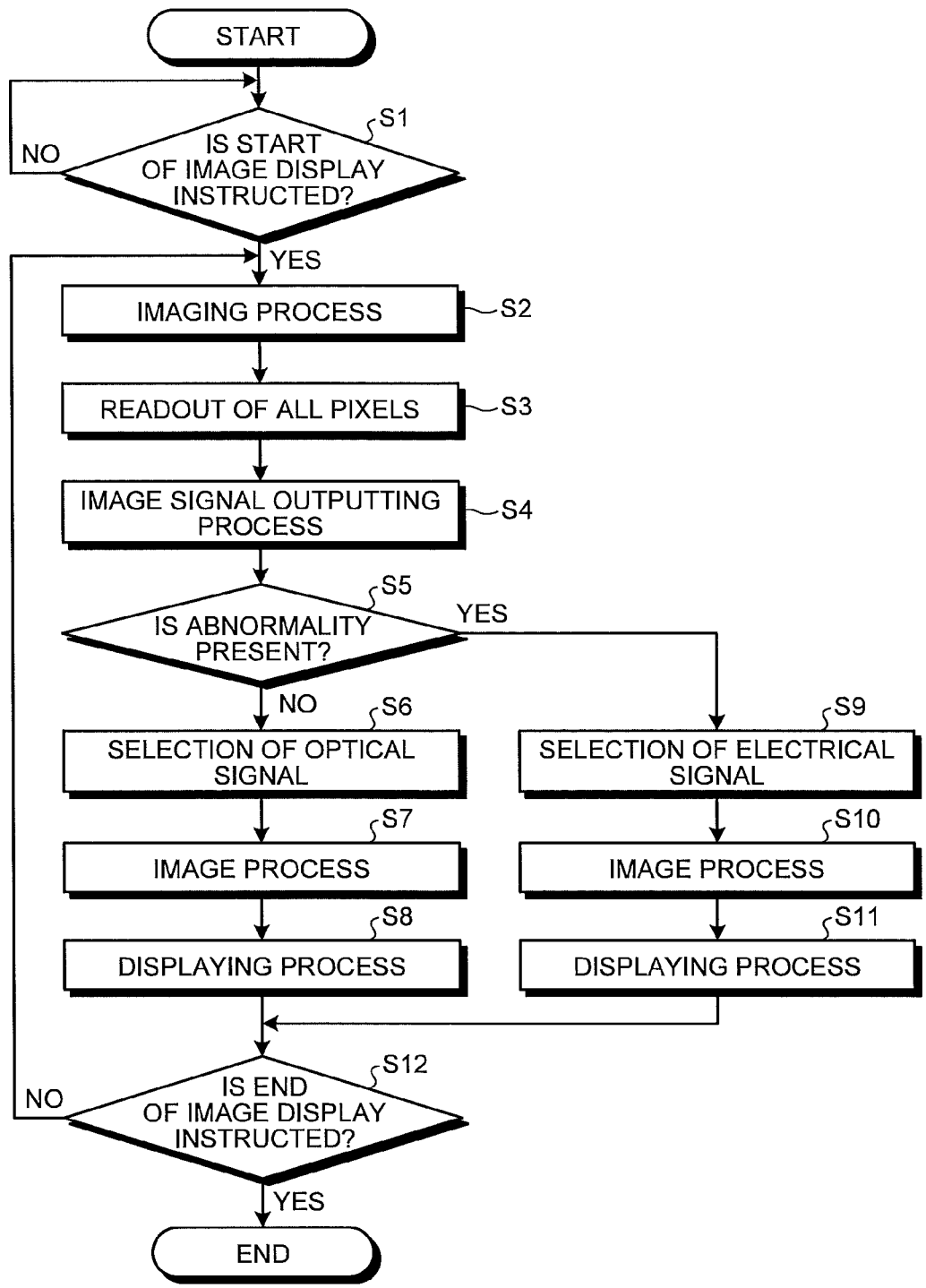
FIG. 8 is a flowchart of a procedure of an in-vivo image displaying process of the endoscope system shown in FIG. 6.

Next, an in-vivo image displaying process of the endoscope system 100 shown in FIG. 6 will be explained. FIG. 8 is a flowchart of a procedure of an in-vivo image displaying process of the endoscope system 100 shown in FIG. 6.

As shown in FIG. 8, the control unit 55 of the control device 40 first determines whether or not an instruction of starting an in-vivo image display is present based on the instruction information input from the input unit 72 and the like (step S1). The control unit 55 repeats the determination process at step S1 until determining that the instruction of starting the in-vivo image display is present.

When determining that the instruction of starting the in-vivo image display is present ("Yes" at step S1), the control unit 55 controls the read-out address setting unit 53, the light modulator 52, and the control circuit 35 to perform the imaging process. The control unit 55 changes a pixel as a read-out target set by the read-out address setting unit 53 so that information of all the pixels within a sensor area Si of the light receiving part 28 is read out in the imaging process. In the distal end part 5, the light receiving part 28 performs the imaging process in accordance with the light emission timing from the light source device 60 (step S2). The timing generator 34 and the AFE unit 36 perform all pixel reading process in which pixel information is read out from all the pixels of the light receiving part 28 in accordance with a predetermined timing signal (step S3). An image signal outputting process in which image signals corresponding to the pixel information of all the read pixels are output from the distal end part 5 to the control device 40 is then performed (step S4). In this image signal outputting process, the read pixel information is transmitted, through branching by the branching unit 81 to the line R1 and the line R2, from both of the optical fiber cable 31 and the electrical cable 32*a*. Image signals to be transmitted from the optical fiber cable 31 correspond to all the pixels of the light receiving part 28 and image signals to be transmitted from the electrical cable 32*a* correspond to partial pixels extracted from all the pixels of the light receiving part 28.

Next, the control unit 55 determines whether or not a transmission abnormality is present in the optical fiber cable 31 based on the presence of the reception of the image signals transmitted from the optical fiber cable 31 (step S5). When the signals cannot be received from the optical fiber cable 31, the control unit 55 determines that an abnormality such as a break of the line has occurred. When the signals can be received from the optical fiber cable 31, the control unit 55 determines that no transmission abnormality is present in the optical fiber cable 31.

When determining that the transmission abnormality is not present in the optical fiber cable 31 ("No" at step S5), the control unit 55 outputs a control signal of instructing a selection of the pixel information transmitted from the optical fiber cable 31 to the selector 58 to cause the selector 58 to select and output image signals from the optical signals transmitted from the optical fiber cable 31 (step S6). The image processor 42 performs an image processing in which the pixel information corresponding to all the pixels transmitted from the optical fiber cable 31 is processed and one high definition image in response to a demand for high definition is generated (step S7). The display unit 71 displays the high definition image generated by the image processor 42 (step S8). Here, the high definition image is as high in level as hundreds of thousands of pixels, for example.

In contrast, when determining that the transmission abnormality is present in the optical fiber cable 31 ("Yes" at step S5), the control unit 55 outputs a control signal of instructing a selection of the pixel information transmitted from the electrical cable 32*a* to the selector 58 to cause the selector 58 to select and output image signals from the electrical signals transmitted from the electrical cable 32*a* (step S9) since no image signal can be obtained by way of the optical fiber cable 31. The image processor 42 performs an image process in which pixel information corresponding to the partial pixels, among all the pixels, transmitted from the electrical cable 32*a* is processed and one image is generated (step S10). The display unit 71 displays the image generated by the image processor 42 (step S11). On this occasion, the image generated by the image processor 42 is a decimated image which is generated based on the pixel information of the partial pixels extracted at predetermined intervals from all the pixels. The decimated image is, for example, as high in level as one hundred thousand pixels, being high enough to be used for the observation.

After ending the displaying process at step S8 or S11, the control unit 55 determines whether or not an end of the image display is instructed based on the instruction information input from the input unit 72 and the like (step S12). When determining that the end of the image display is instructed ("Yes" at step S12), the control unit 55 ends the image displaying process. On the other hand, when determining that the end of the image display is not instructed ("No" at step S12), the control unit 55 returns to step S2 and performs the imaging process to obtain a next frame image.

As explained, the electrical cable 32*a* is provided in addition to the optical fiber cable 31 as a transmitter that transmits pixel information output by the light receiving part 28 and pixel information of all the pixels transmitted from the optical fiber cable 31 is selected to generate and display a high definition image when a transmission abnormality is not present in the optical fiber cable 31 in the endoscope system 100 according to the first embodiment. Then, since pixel information transmitted from the electrical cable 32*a* is selected to generate an image when a transmission abnormality such as a break of line occurs in the optical fiber cable 31, it is possible in the endoscope system 100 to make a compensation by the signal transmission by the electrical cable 32*a* and to appropriately continue the image display without cease even when there occurs a break of line and the like in the optical fiber cable 31.

First Modification of First Embodiment

Figure 9:
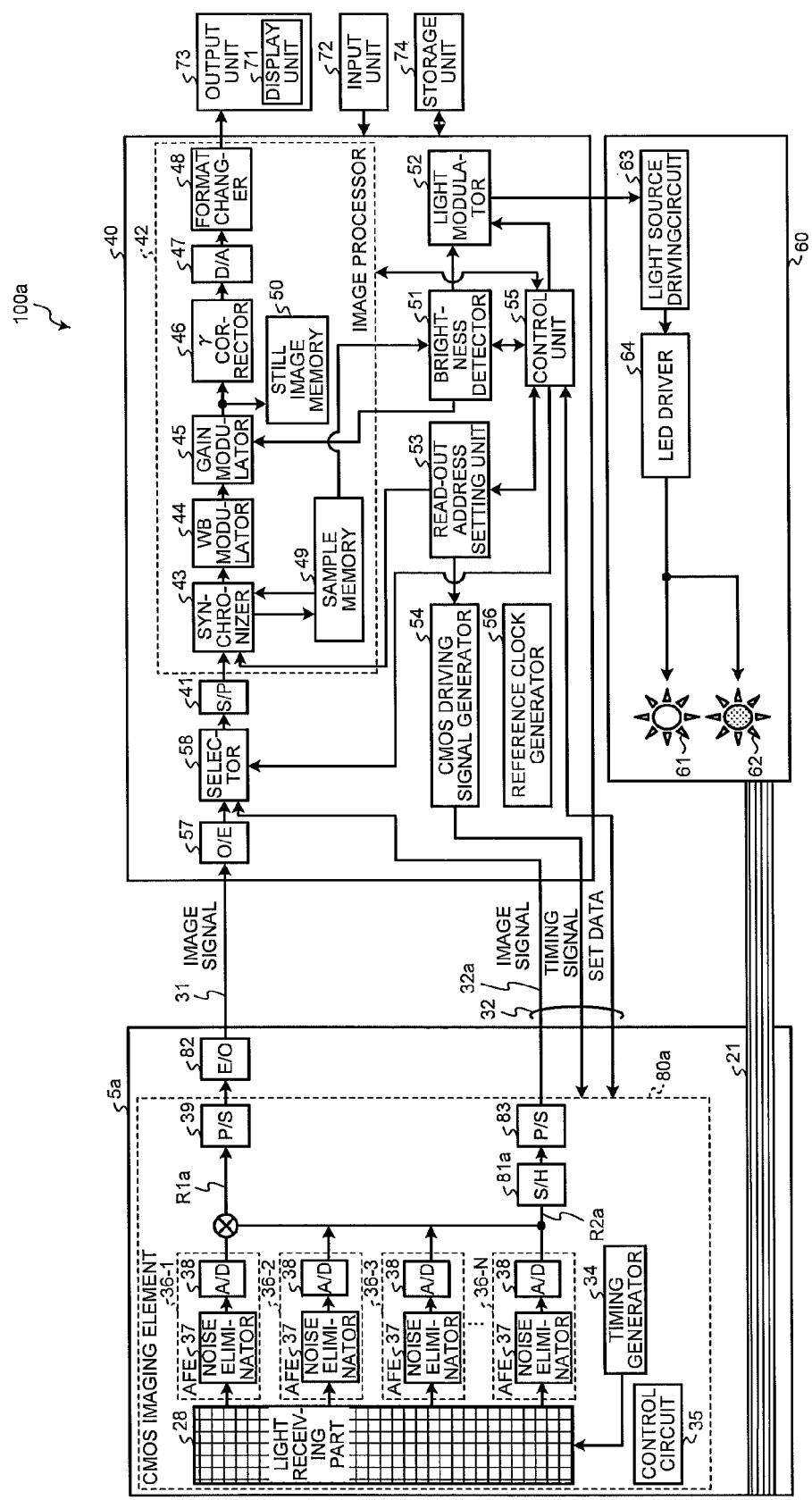
FIG. 9 is a block diagram of a structure of an endoscope system according to a first modification of the first embodiment.

Next, a first modification of the first embodiment will be explained. FIG. 9 is a block diagram of a structure of an endoscope system according to a first modification of the first embodiment. As shown in FIG. 9, AFE units 36-1 to 36-N are provided for respective liens in a CMOS imaging element 80*a* of a distal end part 5*a* in an endoscope system 100*a* according to the first embodiment.

Each of the AFE units 36-1 to 36-N outputs, after performing a noise elimination process and an A/D conversion process on pixel information output at a predetermined timing by the light receiving part 28, the converted digital signal to a line R1a connected to the optical fiber cable 31. The pixel information output from a part (the AFE unit 36-N in FIG. 9) of the plurality of AFE units 36 is then output to the line R1a and also to a line R2a which branches off from the line R1a and is connected to the electrical cable 32a. An S/H circuit 81a extracts part of pixel information for one line output by the AFE unit 36-N which is the part after branching and outputs the extracted information to the P/S converter 83.

Like the endoscope system 100a, a line structure may be set such that the AFE units 36-1 to 36-N are provided for respective lines and a signal from the AFE unit 36-N corresponding to a line as an extraction target is output to both of the line R1a and the line R2a.

Second Modification of First Embodiment

Figure 10:
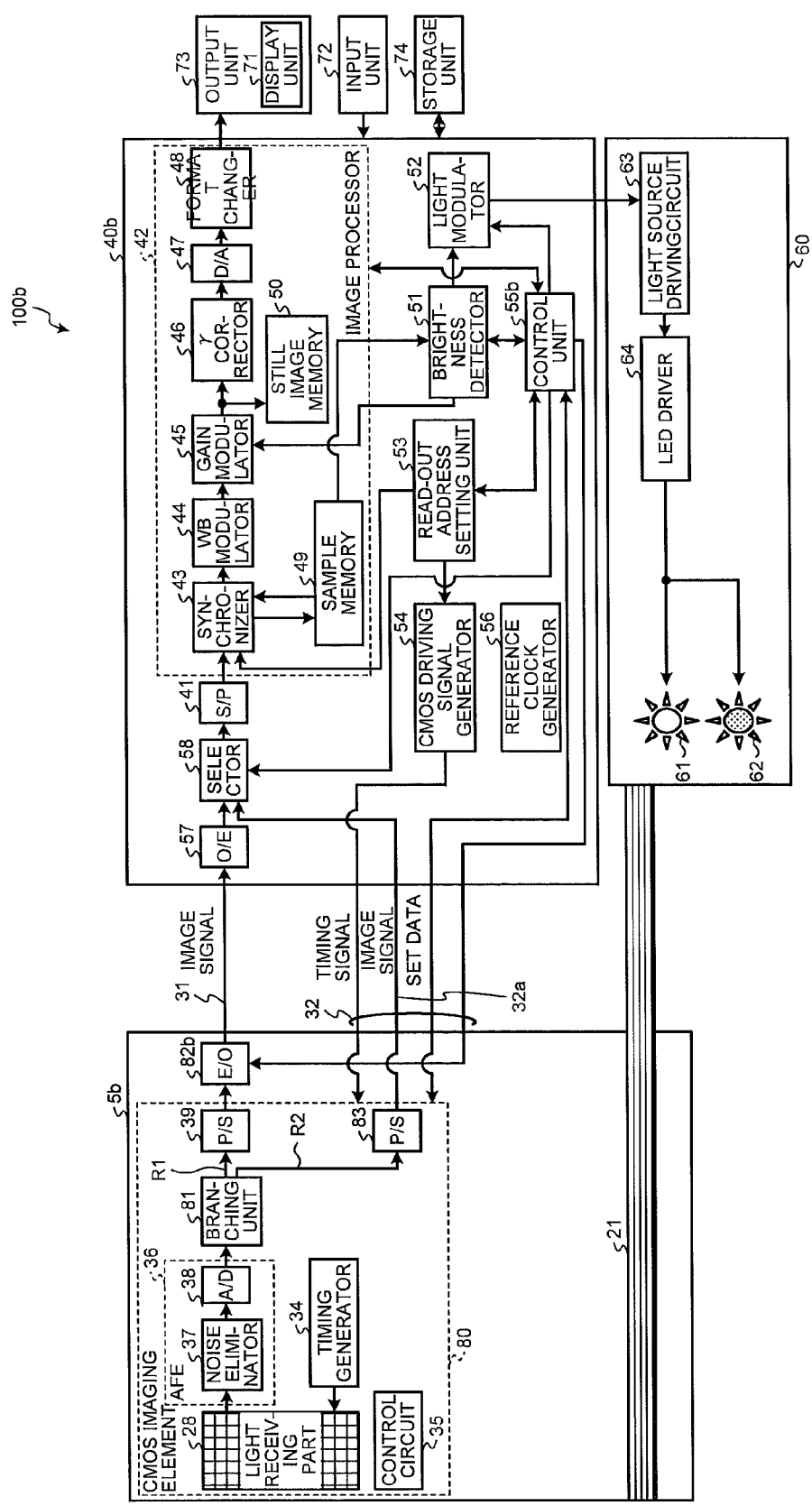
FIG. 10 is a block diagram of a structure of an endoscope system according to a second modification of the first embodiment.

Next a second modification of the first embodiment will be explained. FIG. 10 is a block diagram of a structure of an endoscope system according to a second modification of the first embodiment. As shown in FIG. 10, an E/O converter 82b that has the same function as the E/O converter 82 and also has a function of stopping an output of pixel information output by the CMOS imaging element 80 to the optical fiber cable 31 is provided at a distal end part 5b, instead of the E/O converter 82 shown in FIG. 6.

A control unit 55b of a control device 40b has the same function as the control unit 55 shown in FIG. 6 and also controls the E/O converter 82b to stop the output of pixel information output by the CMOS imaging element 80 to the optical fiber cable 31 when a transmission abnormality is present in the optical fiber cable 31.

Figure 11:
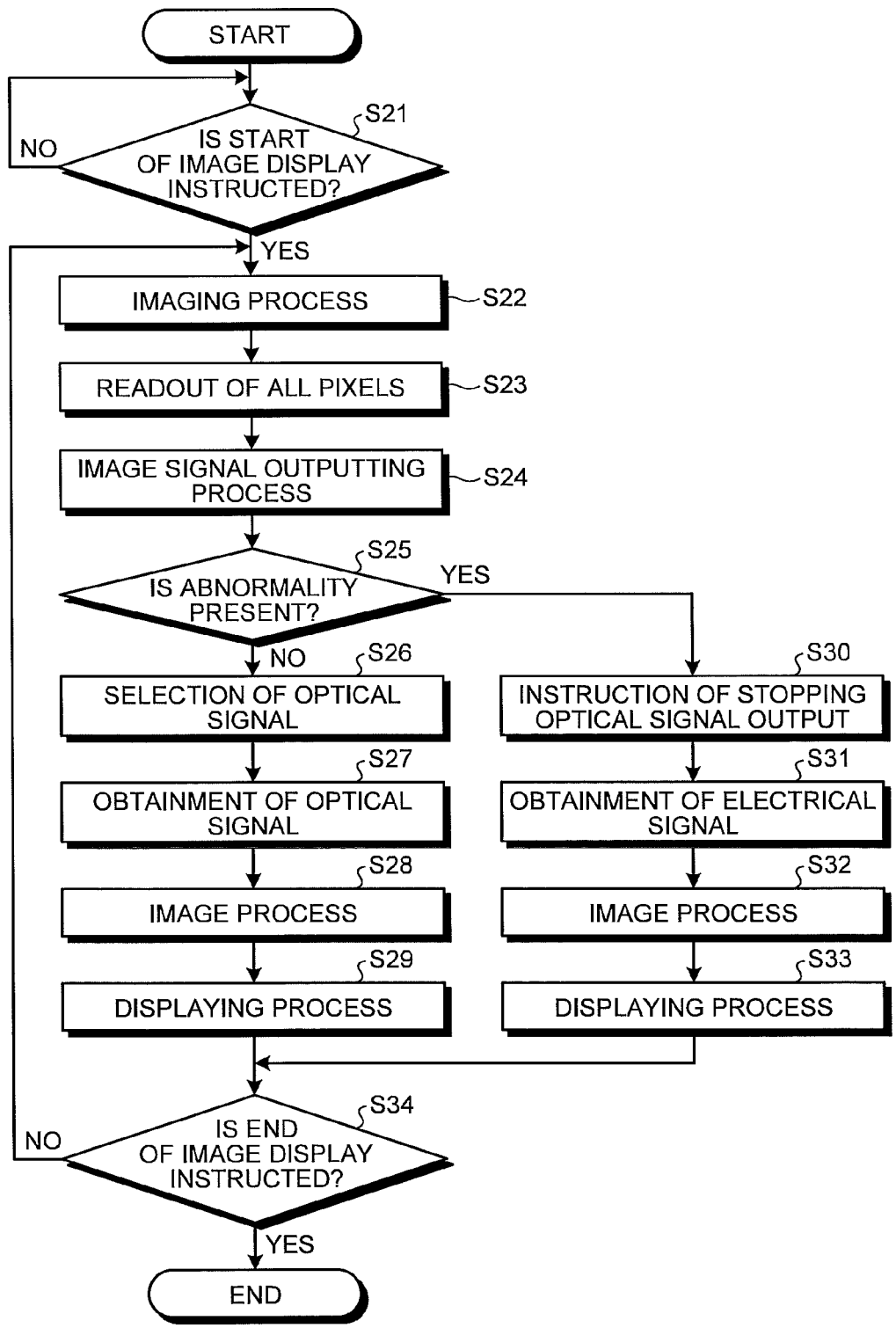
FIG. 11 is a flowchart of a procedure of an in-vivo image displaying process of the endoscope system shown in FIG. 10.

Next, an in-vivo image displaying process of an endoscope system 100b shown in FIG. 10 will be explained. FIG. 11 is a flowchart of a procedure of an in-vivo image displaying process of the endoscope system 100b shown in FIG. 10.

As shown in the flowchart in FIG. 11, the control unit 55b of the control device 40b determines whether or not an instruction of starting an in-vivo image display is present similarly to step S1 shown in FIG. 8 (step S21). The control unit 55b repeats the determination process at step S21 until determining that the instruction of starting the in-vivo image display is present.

When the control unit 55b determines that the instruction of starting the in-vivo image display is present ("Yes" at step S21), an imaging process in the light receiving part 28 (step S22), all pixel reading process with respect to all the pixels of the light receiving part 28 by the timing generator 34 and the AFE unit 36 (step S23), an image signal outputting process with respect to image signals corresponding to the read pixel information (step S24) are performed similarly to steps S2 to S4 shown in FIG. 8. In the image signal outputting process, the read pixel information is output to the line R1 and also to the branching line R2 in the branching unit 81 and transmitted from both of the optical fiber cable 31 and the electrical cable 32a.

Next, the control unit 55b determines whether or not a transmission abnormality is present in the optical fiber cable 31 similarly to step S5 shown in FIG. 8 (step S25). When determining that the transmission abnormality is not present in the optical fiber cable 31 ("No" at step S25), the control unit 55b controls the selector 58 to select and output image signals from the optical signals transmitted from the optical fiber cable 31 similarly to the first embodiment (step S26). The image processor 42 then obtains pixel information from the optical signals corresponding to all the pixels transmitted from the optical fiber cable 31 (step S27) and performs the image process of generating one high definition image based on the obtained pixel information (step S28). The display unit 71 displays the high definition image generated by the image processor 42 (step S29).

In contrast, when determining that the transmission abnormality is present in the optical fiber cable 31 ("Yes" at step S25), the control unit 55b outputs a control signal of instructing a stop of outputting information to the optical fiber cable 31 to the E/O converter 82b of the distal end part 5b (step S30) to control the E/O converter 82b to stop outputting the pixel information output by the CMOS imaging element 80 to the optical fiber cable 31. As a result of this, the E/O converter 82b stops the conversion process and the output process. Here, only image signals corresponding to the pixel information transmitted from the electrical cable 32a are configured to be input to the image processor 42 of the control device 40b. Therefore, the image processor 42 directly obtains electrical signals corresponding to the partial pixels, among all the pixels, transmitted from the electrical cable 32a (step S31) and performs the image process of generating one decimated image (step S32). After that, the display unit 71 displays the decimated image generated by the image processor 42 (step S33).

After ending the displaying process at step S29 or S33, the control unit 55b determines whether or not an end of the image display is instructed similarly to step S12 shown in FIG. 8 (step S34). When determining that the end of the image display is instructed ("Yes" at step S34), the control unit 55b ends the image displaying process. On the other hand, when determining that the end of the image display is not instructed ("No" at step S34), the control unit 55b returns to step S22 and performs the imaging process to obtain a next frame image. Since a screen is generated based on electrical signals corresponding to the partial pixels, transmitted from the electrical cable 32a, of all the pixels when the transmission abnormality in the optical fiber cable 31 continues, it becomes possible to appropriately continue the image display without cease. Besides, since the conversion process and the output process are stopped in the E/O converter 82b when the transmission abnormality is present in the optical fiber cable 31, it is also possible to save an electric power and reduce a heat generation in the distal end part 5b.

Third Modification of First Embodiment

Figure 12:
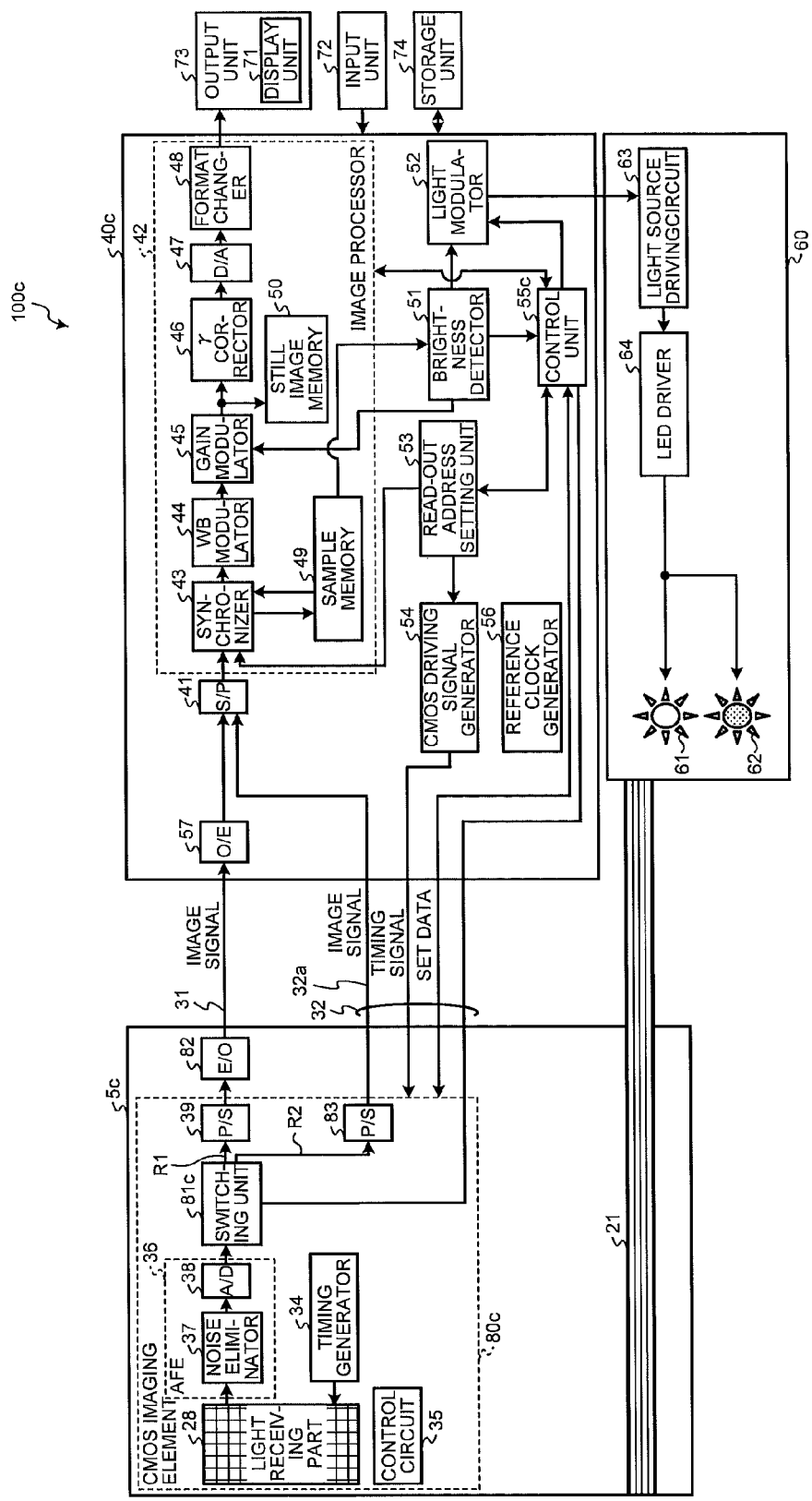
FIG. 12 is a block diagram of a structure of an endoscope system according to a third modification of the first embodiment.
Figure 13:
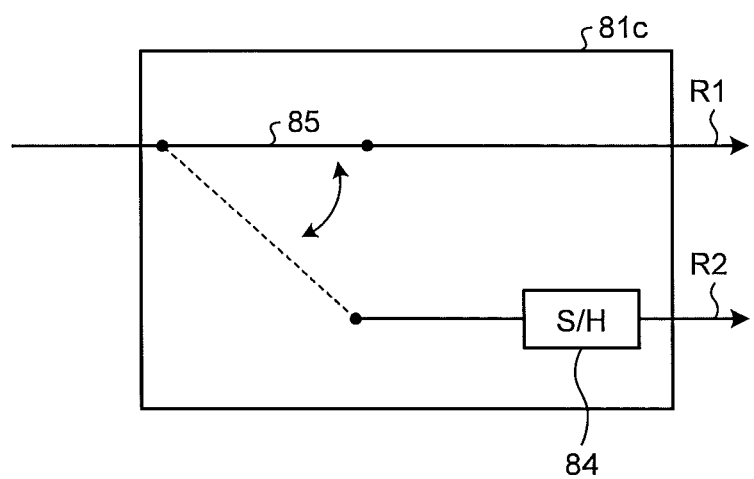
FIG. 13 is an explanatory view of a structure of the switching unit shown in FIG. 12.

Next, a third modification of the first embodiment will be explained. FIG. 12 is a block diagram of a structure of an endoscope system according to a third modification of the first embodiment. As shown in FIG. 12, a switching unit 81c is provided in a CMOS imaging element 80c of a distal end part 5c, instead of the branching unit 81 shown in FIG. 6 in an endoscope system 100c according to the first embodiment. The switching unit 81c is provided with a switch 85 that switches a destination of outputting the pixel information output by the light receiving part 28 via the AFE unit 36 to one of the line R1 side connected to the optical fiber cable 31 and the line R2 side connected to the electrical cable 32a as shown in FIG. 13. Here, the line R2 is connected to the S/H circuit 84 in the switching unit 81c, similarly to the branching unit 81.

A control unit 55c of a control device 40c has the same function as the control unit 55 shown in FIG. 6. When the transmission abnormality is not present in the optical fiber cable 31, the control unit 55c controls the switching unit 81c to cause the switch 85 to switch the destination of outputting the pixel information output by the light receiving part 28 via the AFE unit 36 to the line R1 side connected to the optical fiber cable 31. When the transmission abnormality is present in the optical fiber cable 31, the control unit 55*c* controls the switching unit 81*c* to cause the switch 85 to switch the destination of outputting the pixel information output by the light receiving part 28 via the AFE unit 36 to the electrical cable 32*a*. Here, the control device 40*c* has a configuration in which the selector 58 is eliminated, compared to the control device 40 shown in FIG. 6.

Figure 14:
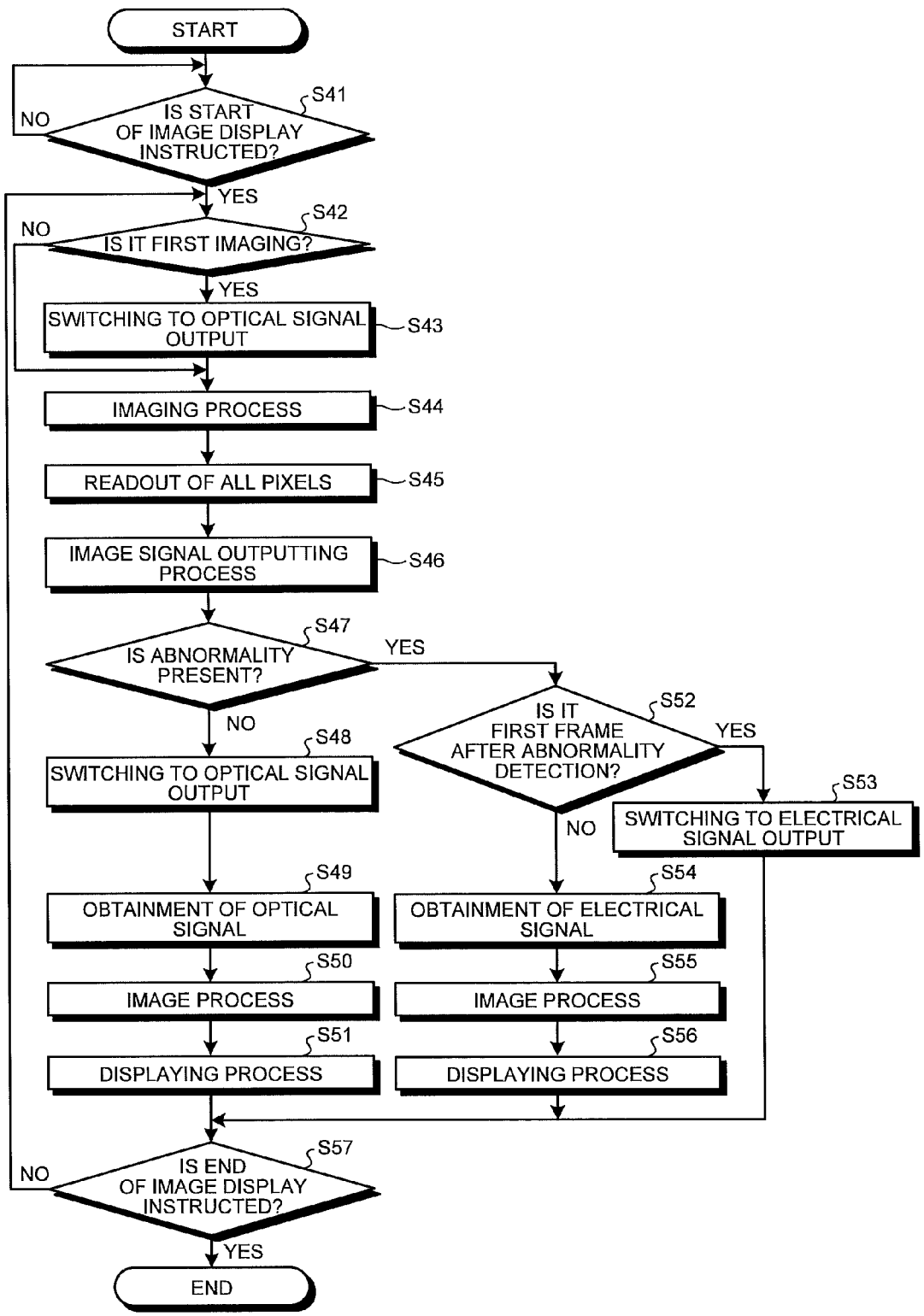
FIG. 14 is a flowchart of a procedure of an in-vivo image displaying process of the endoscope system shown in FIG. 12.

Next, an in-vivo image displaying process of the endoscope system 100*c* shown in FIG. 12 will be explained. FIG. 14 is a flowchart of a procedure of an in-vivo image displaying process of the endoscope system 100*c* shown in FIG. 12.

As shown in the flowchart in FIG. 14, the control unit 55*c* of the control device 40*c* first determines whether or not an instruction of starting an in-vivo image display is present similarly to step S1 shown in FIG. 8 (step S41). The control unit 55*c* repeats the determination process at step S41 until determining that the instruction of starting the in-vivo image display is present.

When the control unit 55*c* determines that the instruction of starting the in-vivo image display is present ("Yes" at step S41), the control unit 55*c* determines whether or not it is the first imaging process (step S42). When determining that it is the first imaging process ("Yes" at step S42), the control unit 55*c* outputs, to the switching unit 81*c*, a control signal of switching the destination of outputting the pixel information output by the light receiving part 28 via the AFE unit 36 to the line R1 side connected to the optical fiber cable 31 to switch the output of the image signals to an optical signal output to attempt the high definition image output (step S43).

When the control unit 55*c* determines that it is not the first imaging process ("No" at step S42) or when the switching process at step S43 is ended, the imaging process in the light receiving part 28 (step S44), the all pixel reading process with respect to all the pixels of the light receiving part 28 by the timing generator 34 and the AFE unit 36 (step S45), and the image signal outputting process with respect to image signals corresponding to the read pixel information (step S46) are performed similarly to steps S2 to S4 shown in FIG. 8. In the image signal outputting process, the read pixel information is transmitted from the optical fiber cable 31 to the control device 40*c* by way of the line R1 to which the switching unit 81*c* has switched when it is the first imaging process.

Next, the control unit 55*c* determines whether or not a transmission abnormality is present in the optical fiber cable 31 similarly to step S5 shown in FIG. 8 (step S47). When determining that the transmission abnormality is not present in the optical fiber cable 31 ("No" at step S47), the control unit 55*c* performs the procedure similar to step S43 to switch to the optical signal output in the case where the output of image signals is switched to the line R2 at the side of the electrical cable 32*a* (step S48). Here, when the optical signal output is held, the optical signal output is made to continue. In this case, the image processor 42 directly obtains pixel information from the optical signals transmitted form the optical fiber cable 31 (step S49) and performs the image process of generating one high definition image (step S50), and the display unit 71 displays the high definition image generated by the image processor (step S51).

On the other hand, when determining that the transmission abnormality is present in the optical fiber cable 31 ("Yes" at step S47), the control unit 55*c* determines whether or not the imaging process this time deals with the first frame image after the abnormality was detected (step S52).

When determining that the imaging process this time deals with the first frame image ("Yes" at step S52), for continuing the image display, the control unit 55*c* outputs, to the switching unit 81*c*, a control signal of switching the destination of outputting the pixel information output by the light receiving part 28 via the AFE unit 36 to the line R2 connected to the electrical cable 32*a* to switch the output of image signals from the optical signal output to the electrical signal output (step S53). Since image signals cannot be received in the imaging process this time due to the transmission abnormality in the optical fiber cable 31, the image process and the image displaying process are not performed and the process moves directly to step S57.

When the control unit 55*c* determines that the imaging process this time does not deal with the first frame image after the abnormality was detected ("No" at step S52), the image processor 42 directly obtains the electrical signals transmitted from the electrical cable 32*a* since the output of the image signals is already switched from the optical signal output to the electrical signal output in the first frame after the abnormality was detected (step S54) and performs the image process of generating one decimated image (step S55), and the display unit 71 displays the decimated image generated by the image processor 42 (step S56).

After ending the displaying process at step S51 or S56, or after the switching to the electrical signal output at step S53, the control unit 55*c* determines whether or not an end of the image display is instructed similarly to step S12 shown in FIG. 8 (step S57). When determining that the end of the image display is instructed ("Yes" at step S57), the control unit 55*c* ends the image displaying process.

On the other hand, when determining that the end of the image display is not instructed ("No" at step S57), the control unit 55*c* returns to step S42 and determines whether or not it is the first imaging process (step S42). Since the optical signal output is maintained when the transmission abnormality is not present in the optical fiber cable 31, the imaging process (step S44) and the all pixel reading process (S45) are performed and the control unit 55*c* again determines, after image signals corresponding to all the pixels of the light receiving part 28 are output in a form of an optical signal from the optical fiber cable 31 (step S46), whether or not the transmission abnormality is present in the optical fiber cable 31 (step S47).

Since the output is switched to the electrical signal output when the transmission abnormality is present in the optical fiber cable 31, the imaging process (step S44) and the all pixel reading process (S45) are performed and the control unit 55*c* again determines, after image signals corresponding to partial pixels extracted from all the pixels of the light receiving part 28 are output in a form of an electrical signal from the electrical cable 32*a* (step S46), whether or not the transmission abnormality is present in the optical fiber cable 31 (step S47). Here, when the control unit 55*c* determines that the transmission abnormality keeps continuing in the optical fiber cable 31 ("Yes" at step S47), steps S52 to S56 are performed and a decimated image is displayed. On the other hand, when the control unit 55*c* determines that the transmission abnormality has made a recovery into a normal state in the optical fiber cable 31 ("No" at step S47), the output is switched from the electrical signal output to the optical signal output, and a high definition image is displayed.

As explained, it is possible according to the third modification of the first embodiment to continue the image display even when the transmission abnormality has occurred in the optical fiber cable 31, similarly to the first embodiment. In addition, it is possible according to the third modification of the first embodiment to save an electric power and reduce a heat generation more than the first embodiment since there becomes no necessity of performing the conversion process every time in both of the P/S converters 39 and 83 by completely switching the destination of outputting signals to one of the line R1 side connected to the optical fiber cable 31 and the line R2 side connected to the electrical cable 32a in the distal end part 5c.

While an example of using the CMOS imaging element as an imaging element is explained in the first embodiment and the first to the third modifications of the first embodiment, the present invention can be, of course, applied to a case of using a CCD imaging element.

Second Embodiment

Next, a second embodiment will be explained. In a second embodiment, a case where a pixel as a read-out target of the CMOS imaging element is changed from all the pixels to a part of the pixels and pixel information of the read partial pixels is transmitted by using the electrical cable when a transmission abnormality is present in the optical fiber cable will be explained.

Figure 15:
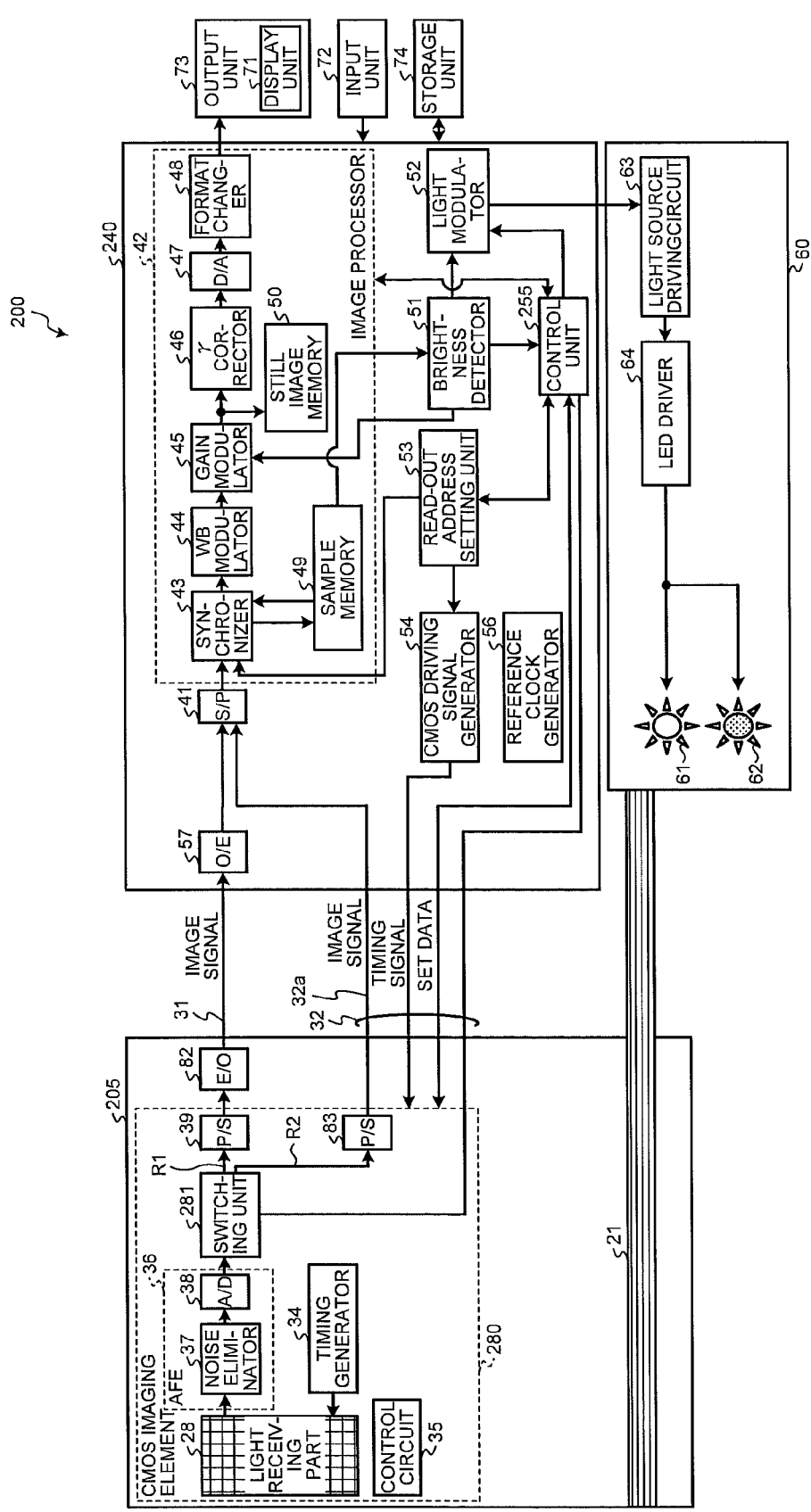
FIG. 15 is a block diagram of a structure of an endoscope system according to a second embodiment.

FIG. 15 is a block diagram of a structure of an endoscope system according to the second embodiment. As shown in FIG. 15, a distal end part 205 including a CMOS imaging element 280 is provided instead of the distal end part 5 shown in FIG. 6 in an endoscope system 200 according to the second embodiment. The endoscope system 200 is provided, instead of the control device 40 shown in FIG. 6, with a control device 240 including a control unit 255 having the same function as the control unit 55. The control device 240 has a configuration in which the selector 58 shown in FIG. 6 is eliminated.

Figure 16:
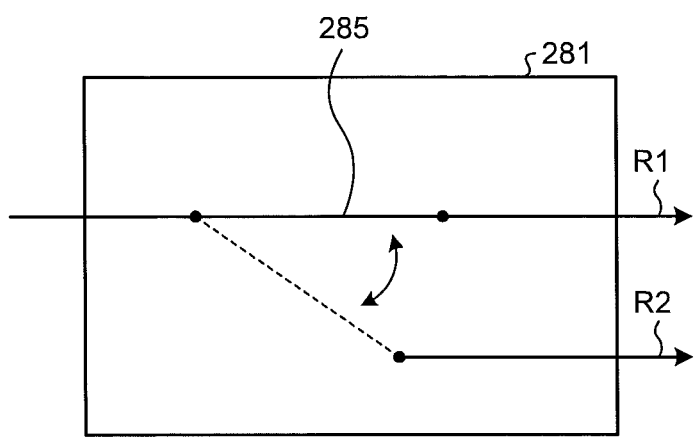
FIG. 16 is an explanatory view of a structure of the switching unit shown in FIG. 15.

The CMOS imaging element 280 is provided with a switching unit 281 instead of the branching unit 81 shown in FIG. 6. As shown in FIG. 16, the switching unit 281 is provided with a switch 285 that is capable of switching the destination of outputting pixel information output by the light receiving part 28 to one of the line R1 connected to the optical fiber 31 and the line R2 connected to the electrical cable 32a under the control by the control unit 255.

The control unit 255 controls the switching unit 281 to cause the switch 285 of the switching unit 281 to switch the destination of outputting the pixel information output by the light receiving part 28 to the line R1 connected to the optical fiber cable 31 when the transmission abnormality is not present in the optical fiber cable 31. Besides, when the transmission abnormality is present in the optical fiber cable 31, the control unit 255 makes a change of a pixel as a read-out target so that the pixel as a read-out target set by the read-out address setting unit 53 is changed to partial pixels extracted from all the pixels of the light receiving part 28, and controls the switching unit 281 to cause the switch 285 of the switching unit 281 to switch the destination of outputting the pixel information output by the light receiving part 28 to the line R2 side connected to the electrical cable 32a when the transmission abnormality is present in the optical fiber cable 31. Therefore, when the transmission abnormality occurs in the optical fiber cable 31, image signals corresponding to the pixel information of the partial pixels extracted from all the pixels of the light receiving part 28 are output to the control device 240 by way of the electrical cable 32a.

Figure 17:
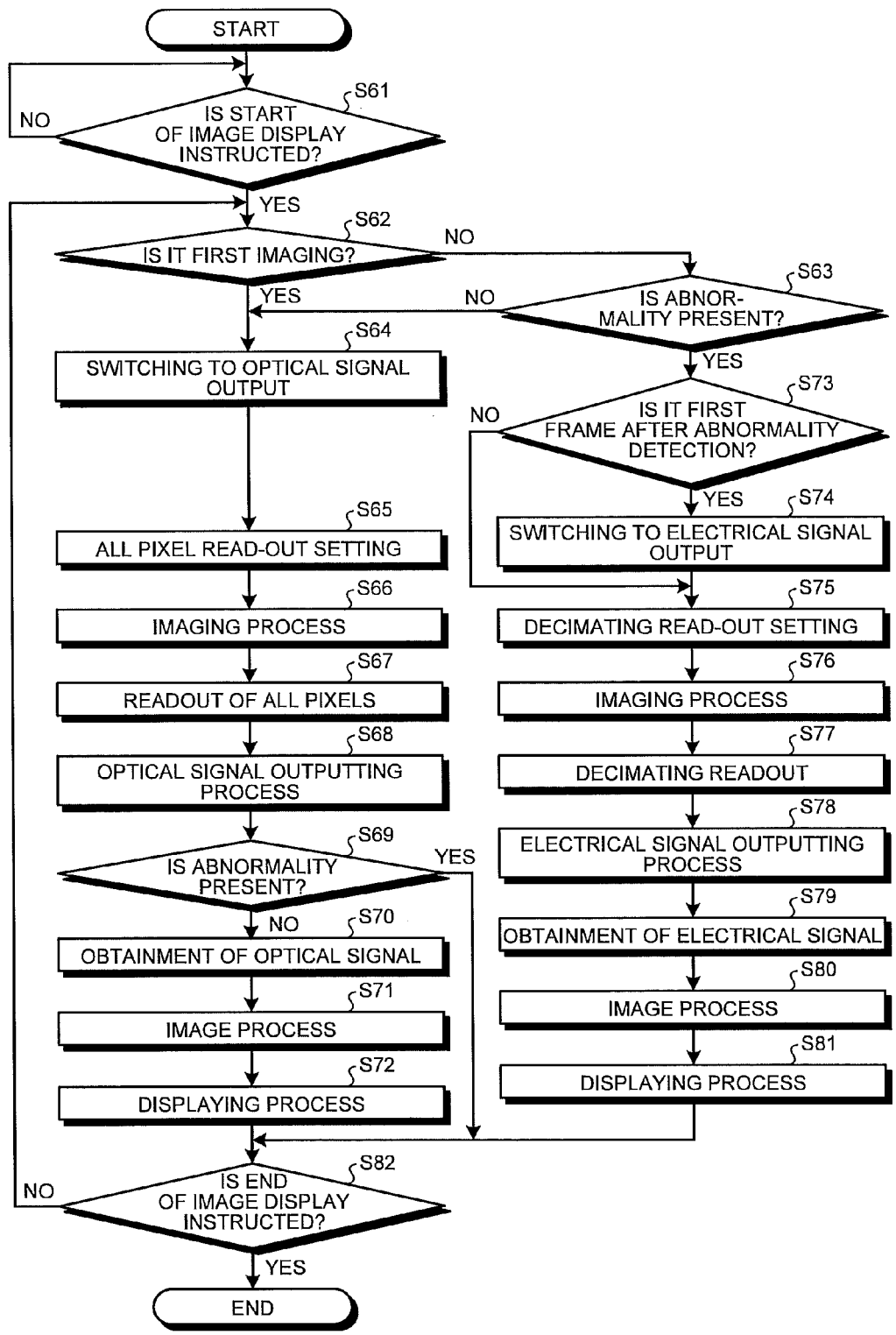
FIG. 17 is a flowchart of a procedure of an in-vivo image displaying process of the endoscope system shown in FIG. 15.

Next, an in-vivo image displaying process of the endoscope system 200 shown in FIG. 15 will be explained. FIG. 17 is a flowchart of a procedure of an in-vivo image displaying process of the endoscope system 200 shown in FIG. 15.

As shown in the flowchart in FIG. 17, the control unit 255 of the control device 240 first determines whether or not an instruction of starting an in-vivo image display is present similarly to step S1 shown in FIG. 8 (step S61). The control unit 255 repeats the determination process at step S61 until determining that the instruction of starting the in-vivo image display is present.

When the control unit 255 determines that the instruction of starting the in-vivo image display is present ("Yes" at step S61), the control unit 255 determines whether or not it is the first imaging process (step S62). When determining that it is the first imaging process ("Yes" at step S62), the control unit 255 first outputs, to the switching unit 281, a control signal of switching the destination of outputting the pixel information output by the light receiving part 28 by way of the AFE unit 36 to the line R1 connected to the optical fiber cable 31 to switch the output of image signals to the optical signal output to attempt the high definition image output (step S64).

When determining that it is not the first imaging process ("No" at step S62), the control unit 255 determines whether or not the transmission abnormality was present in the optical fiber cable 31 in the signal outputting process dealing with the previous imaging process (step S63). When determining that the transmission abnormality was not present in the optical fiber cable 31 in the signal outputting process dealing with the previous imaging process ("No" at step S63), the control unit 255 switches the output of the image signals to the optical signal output (step S64). Here, when the optical signal output is held, the optical signal output continues without change.

To obtain a high definition image, the control unit 255 then performs an all pixel read-out setting process in which the read-out address setting unit 53 is made to set all the pixels of the light receiving part 28 as a read-out target pixel (step S65). Thus, in the distal end part 205, the timing generator 34 and the AFE unit 36 read out, after the light receiving part 28 performs the imaging process at a predetermined timing (step S66), pixel information from all the pixels of the light receiving part 28 (step S67). Image signals corresponding to the pixel information of all the read pixels go through the line R1 to which the switching unit 281 has switched and undergo an optical signal outputting process in which the image signals are converted into optical signals and output to the control device 240 from the optical fiber cable 31 (step S68).

After that, the control unit 255 determines whether or not a transmission abnormality is present in the optical fiber cable 31 in the signal outputting process dealing with the imaging process this time (step S69). When determining that the transmission abnormality is present in the optical fiber cable 31 ("Yes" at step S69), the control unit 255 does not perform the image process and the image displaying process since image signals cannot be received due to the transmission abnormality in the optical fiber cable 31 in the imaging process this time and then moves directly to step S82.

On the other hand, when the control unit 255 determines that the transmission abnormality is not present in the optical fiber cable 31 ("No" at step S69), the image processor 42 directly obtains pixel information from the optical signals transmitted form the optical fiber cable 31 (step S70) and performs the image process of generating one high definition image (step S71), and the display unit 71 displays the high definition image generated by the image processor (step S72).

After ending the displaying process at step S72 or when the control unit 255 determines that the transmission abnormality is present in the optical fiber cable 31 ("Yes" at step S69), the control unit 255 determines whether or not an end of the image display is instructed similarly to step S12 shown in FIG. 8 (step S82). When determining that the end of the image display is instructed ("Yes" at step S82), the control unit 255 ends the image displaying process.

In contrast, when determining that the end of the image display is not instructed ("No" at step S82), the control unit 255 returns to step S62, determines whether or not it is the first imaging process, and then determines, when determining that it is not the first imaging process ("No" at step S62), whether or not the transmission abnormality was present in the optical fiber cable 31 in the signal outputting process dealing with the previous imaging process (step S63). Here, when determining that the transmission abnormality was present in the optical fiber cable 31 in the signal outputting process dealing with the previous imaging process ("Yes" at step S63), the control unit 255 determines whether or not the imaging process this time deals with the first frame image after the abnormality was detected (step S73).

When determining that the imaging process this time deals with the first frame image after the abnormality was detected ("Yes" at step S73), the control unit 255 outputs for attempting the continuation of the image display, to the switching unit 281, a control signal of switching the destination of outputting the pixel information output by the light receiving part 28 by way of the AFE unit 36 to the line R2 connected to the electrical cable 32a, switches the output of image signals from the optical signal output to the electrical signal output (step S74), and moves to step S75.

When determining that the imaging process this time does not deal with the first frame image after the abnormality was detected ("No" at step S73), since the output of the image signals is already switched to the electrical signal output in the first frame after the abnormality was detected, the control unit 255 keeps the electrical signal output continue and moves to step S75.

After that, since it is necessary to obtain a decimated image to keep the image display continue, the control unit 255 performs a decimating read-out setting process in which a pixel as a read-out target set by the read-out address setting unit 53 is changed only to pixels extracted at predetermined intervals from all the pixels of the light receiving part 28 (step S75).

Figure 18:
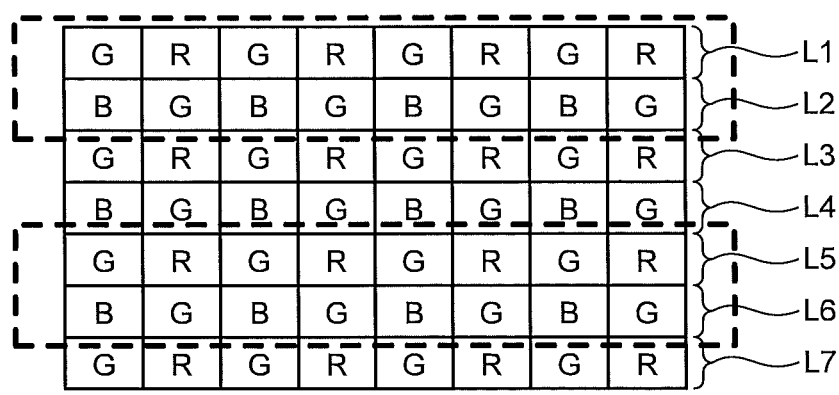
FIG. 18 is an explanatory view of an example of the decimating read-out setting process shown in FIG. 17.
Figure 19:
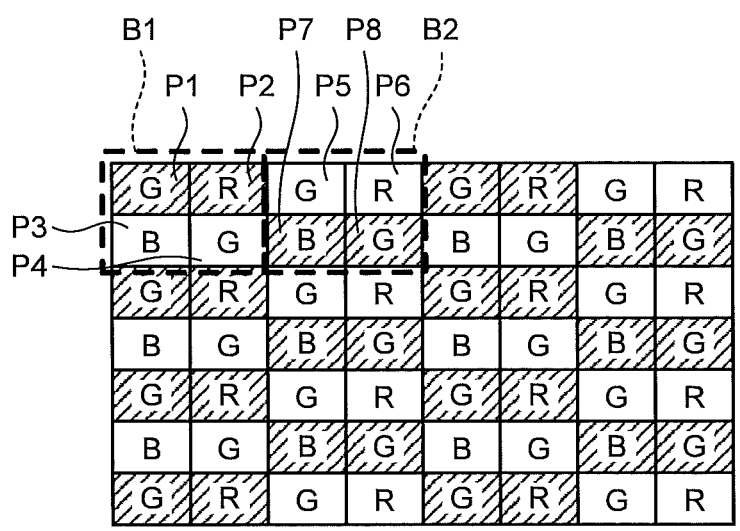
FIG. 19 is an explanatory view of another example of the decimating read-out setting process shown in FIG. 17.

For the decimating read-out setting process, the control unit 255 controls the read-out address setting unit 53 to set each of pixels in lines L1 and L2, and lines L5 and L6 among lines L1 to L7 as a read-out target pixel and read out pixel information every two lines as shown in FIG. 18. In addition to this, the control unit 255 may control the read-out address setting unit 53 to make a setting so that two pixels, i.e., "R, G" or "G, B" are read out alternately. Specifically, as for pixels "R, G, G, B" constituting a block B1, two pixels P1 and P2 for "R, G" are set as a read-out target each and the rest pixels P3 and P4 are treated each as a non-read-out target as shown in FIG. 19. Then, as for a block B2 neighboring the block B1, two pixels P7 and P8 for "B, G" are set as a read-out target each and the rest pixels P5 and P6 are treated each as a non-read-out target. The control unit 255 may, of course, control the read-out address setting unit 53 to set the read-out target pixel so that the reading is performed every two vertical lines, or to divide all the pixels into blocks by treating a predetermined number of, at least four, pixels as one block and set the read-out target pixel by the block unit.

After the light receiving part 28 performs the imaging process at a predetermined timing (step S76), the timing generator 34 and the AFE unit 36 perform the decimating read-out process of reading out pixel information only from partial pixels extracted from all the pixels of the light receiving part 28 in the distal end part 205 (step S77). Then, image signals corresponding to the read partial information in the pixel information of all the pixels go through the line R2 to which the switching unit 281 has switched and undergo the electrical signal outputting process in which the image signals are output to the control device 240 from the electrical cable 32a (step S78). The image processor 42 directly obtains pixel information from the electrical signals transmitted from the electrical cable 32a (step S79) and performs the image process of generating one decimated image (step S80). After the decimated image generated by the image processor 42 is displayed in the display unit 71 (step S81), the process moves to step S82.

As explained, the endoscope system 200 according to the second embodiment has the same advantages as the first embodiment. Besides, it is possible in the endoscope system 200 to make the reading process more efficient compared to the first embodiment since pixel information is read out only from partial pixels appropriate to the decimated-image display when a transmission abnormality occurs in the optical fiber cable 31, and to make a circuit configuration of the CMOS imaging element 280 at the distal end part 205 simple since there is no necessity of providing the S/H circuit in the inside of the CMOS imaging element 280 at the distal end part 205.

Here, image signals to be used for the image process may be selected at the side of the control device 240, similarly to the first embodiment, in the second embodiment and it becomes possible to eliminate the switching unit 281 from the distal end part 205 in this case.

Figure 20:
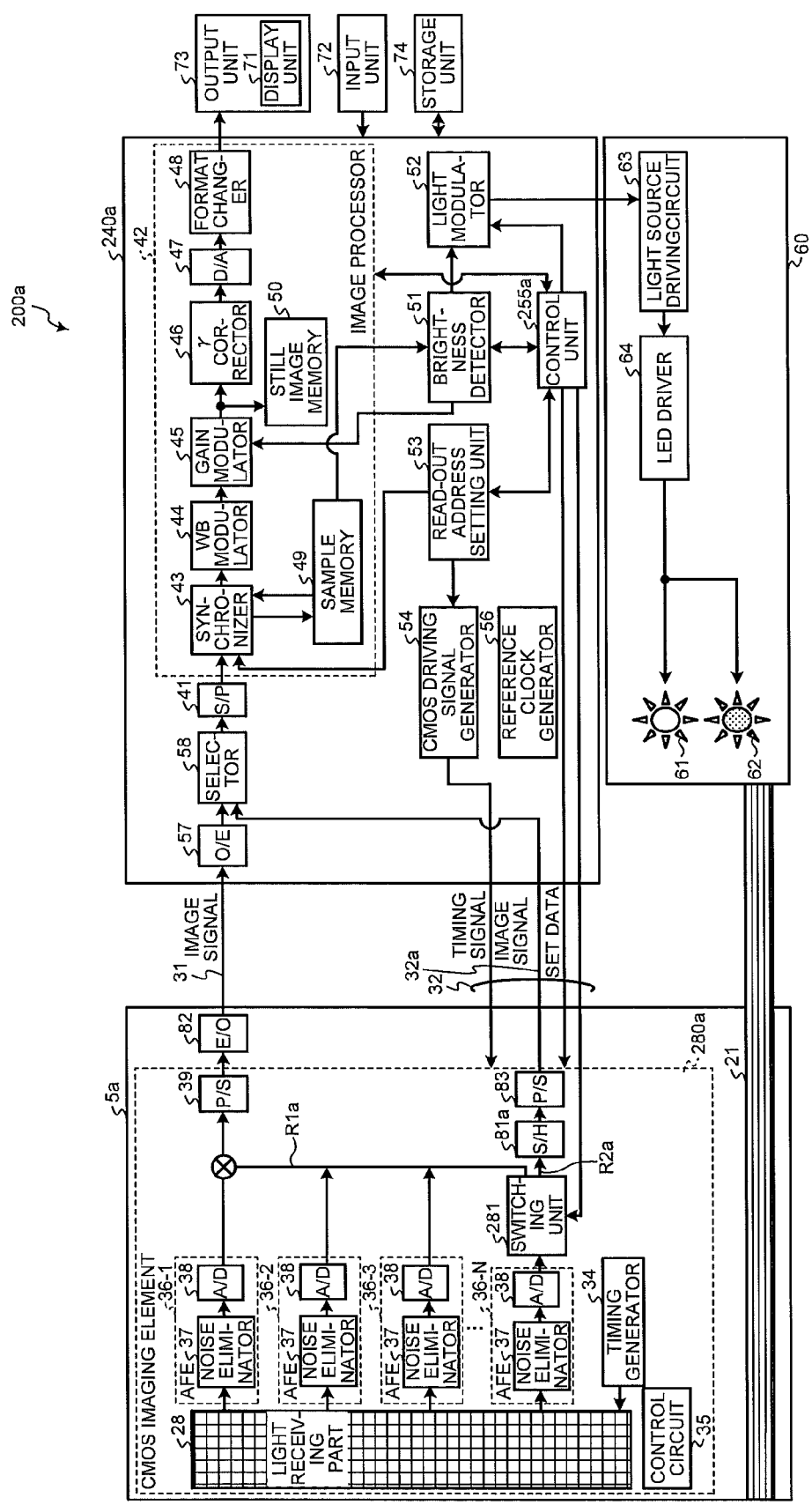
FIG. 20 is a block diagram of another structure of the endoscope system according to the second embodiment.

In addition, a CMOS imaging element 280a provided at a distal end part 205a is provided with a plurality of AFE units 36-1 to 36-N as shown in an endoscope system 200a in FIG. 20 in the second embodiment. In this case, a control unit 255a of a control device 240a changes a line as a read-out target, set by the read-out address setting unit 53, of the CMOS imaging element 280a to a process line for the AFE unit 36-N that can be connected to a line R1a and a line R2a via the switching pat 281 when a transmission abnormality is present in the optical fiber cable 31, and controls the switching unit 281 to switch the output of image signals from the optical signal output to the electrical signal output. Then, an S/H circuit 81a further extracts partial information from the pixel information of the line output from the switching unit 281 and outputs the extracted information to the P/S converter 83, and thus electrical signals corresponding to pixel information read out from the partial pixels extracted from all the pixels of the light receiving part 28 are output from the electrical cable 32a.

First Modification of Second Embodiment

Next, a first modification of the second embodiment will be explained. In a first modification of the second embodiment, a case where pixel information read in the light receiving part is made to branch off before the A/D conversion and output to a control device via one of the optical fiber cable and the electrical cable will be explained.

Figure 21:
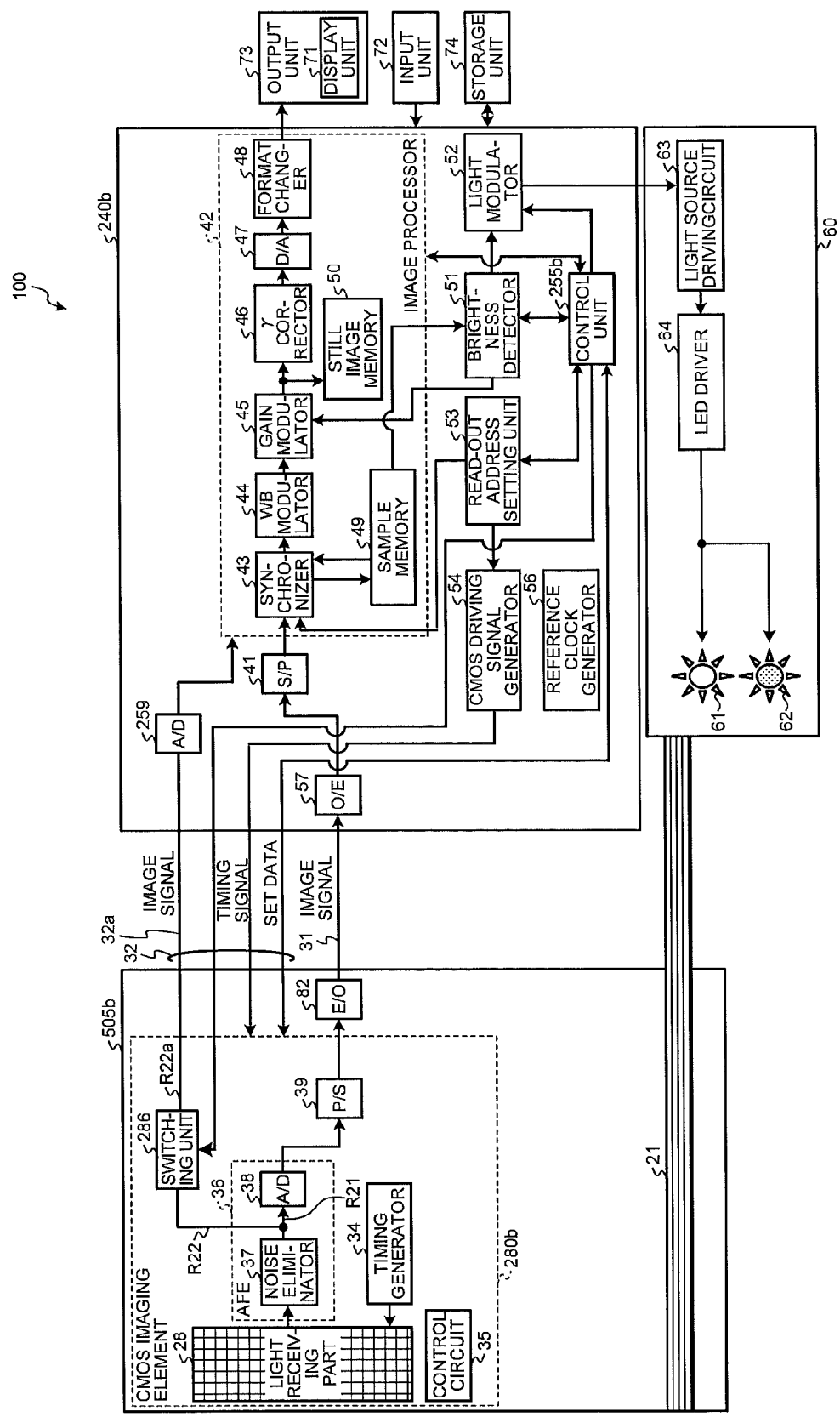
FIG. 21 is a block diagram of a structure of an endoscope system according to a first modification of the second embodiment.

FIG. 21 is a block diagram of a structure of an endoscope system according to a first modification of the second embodiment. As shown in FIG. 21, in an endoscope system 200b according to the first modification of the second embodiment, a distal end part 205b including a CMOS imaging element 280b is provided instead of the distal end part 205 shown in FIG. 15. Besides, the endoscope system 200b is provided, instead of the control device 240 shown in FIG. 15, with a control device 240b including a control unit 255b having the same function as the control unit 255. The control device 240b is provided with an A/D converter 259 that converts an analogue signal output form the electrical cable 32a into a digital signal and outputs the converted signal to the image processor 42.

Figure 22:
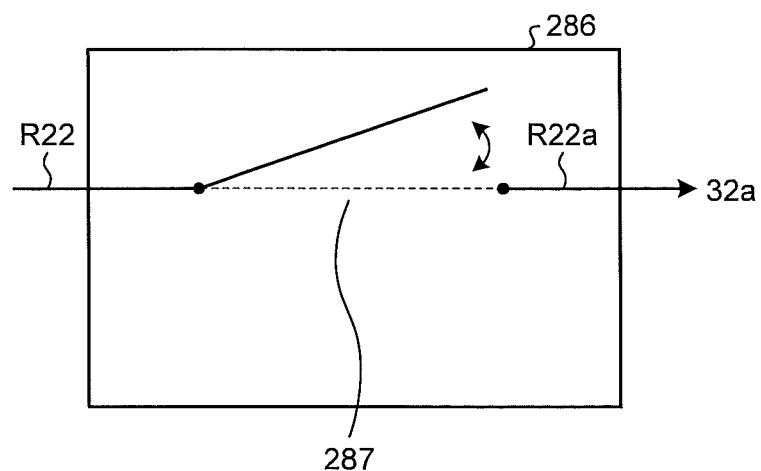
FIG. 22 is an explanatory view of a structure of the switching unit shown in FIG. 21.

The CMOS imaging element 280b has a configuration in which a line R22 branches off from a line R21 between the noise eliminator 37 and the A/D converter 38. The line R22 is connected to a switching unit 286. The switching unit 286 is provided with a switch 287 capable of connecting the line R22 and a line R22a as shown in FIG. 22. Since the line R22a is connected to the electrical cable 32a, it is possible to say that the switching unit 286 is capable of connecting the light receiving part 28 and the electrical cable 32a.

The control unit 255b outputs, to the switching part 286, a control signal of turning off the switch 287 to release the connection between the light receiving part 28 and the electrical cable 32a when a transmission abnormality is not present in a transmission part of the optical fiber cable 31.

When the transmission abnormality is present in the transmitting part of the optical fiber cable 31, the control unit 255b controls the switching unit 286 to change a pixel as a read-out target set by the read-out address setting unit 53 to partial pixels extracted from all the pixels of the light receiving part 28 and to output a control signal of turning on the switch 287 to connect the light receiving part 28 and the electrical cable 32a. Therefore, when the transmission abnormality occurs in the optical fiber cable 31, an analogue corresponding to the pixel information of the partial pixels extracted from all the pixels of the light receiving part 28 is output to the A/D converter 259 of the control device 240b by way of the electrical cable 32a. In the control device 240b, the image processor 42 generates a decimated image based on the electrical signal output from the A/D converter 259 and the display unit 71 then displays the decimated image.

As explained, the endoscope system 200b according to the first modification of the second embodiment has the same advantages as the second embodiment. In the endoscope system 200b, an in-vivo image is displayed by performing the same procedure as the procedure shown in FIG. 17.

Here, it is possible to apply the first and the second embodiments not only to the case where information volume transmitted by the electrical cable 32a is smaller than that transmitted by the optical fiber cable 31 but also to a case where information volume transmitted by the electrical cable 32a is almost equal to that transmitted by the optical fiber cable 31.

Besides, it is possible to apply the first and the second embodiments not only to the case where the electrical cable 32a and the optical fiber cable 31 which are different from each other in a format of transmitting signals are used as a cable that transmits image signals but also to a case where two optical fiber cables or two electrical cables are used.

Figure 23:
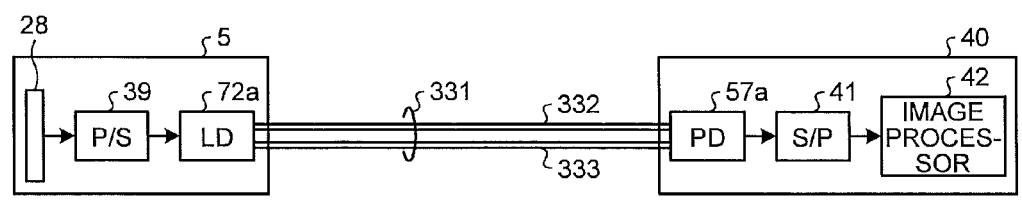
FIG. 23 is an explanatory view of another example of a main part of the optical fiber cable, the distal end part, and the control device shown in FIG. 6.
Figure 24:
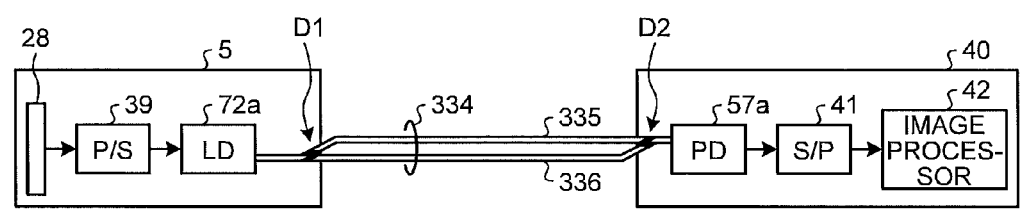
FIG. 24 is an explanatory view of another example of a main part of the optical fiber cable, the distal end part, and the control device shown in FIG. 6.
Figure 25:
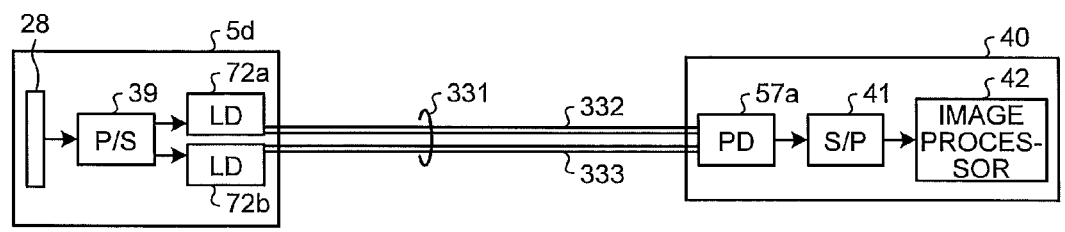
FIG. 25 is an explanatory view of another example of a main part of the optical fiber cable, the distal end part, and the control device shown in FIG. 6.

In the first and the second embodiments, not one optical fiber cable 31 but two optical fiber cables 332 and 333 like an optical signal transmitter 331 in FIG. 23 may be provided to perform the transmission, even in a case where one optical fiber cable breaks, by the other optical fiber cable. In this case, an LD part 72a in the distal end part 5 and a PD part 57a in the control unit 40 joint and couple the two optical fiber cables 332 and 333 into one cable. Moreover, a connection of two optical fiber cables 335 and 336 to the LD part 72a and the PD part 57a may be simplified via a welding at positions D1 and D2 at both ends of the cables like an optical signal transmitter 334 in FIG. 24. Besides, LD parts 72a and 72b respectively for the optical fiber cables 332 and 333 may be provided in a distal end part 5d and a light reception may be made in the PD part 57a at the side of the control device 40 as shown in FIG. 25. In this case, the LD parts 72a and 72b enable a transmission by one half of the frequency of the case having only the LD part 72a.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus, comprising:
   an imaging sensor comprising a light receiving part configured to obtain an electrical signal after a photoelectric conversion from a plurality of pixels for imaging, and to output the electrical signal as pixel information;
   an optical fiber cable that constitutes a first transmission channel, wherein the optical fiber cable is configured to transmit a first pixel information including the pixel information output from the imaging sensor;
   an electrical cable that constitutes a second transmission channel, wherein the electrical cable is configured to transmit a second pixel information including a portion of the pixel information output from the imaging unit;
   a first receiver configured to receive the first pixel information transmitted by the optical fiber cable;
   a second receiver configured to receive the second pixel information transmitted by the second transmitter;
   a selection circuit configured to select one of the first pixel information and the second pixel information;
   a control circuit configured to determine whether or not a transmission abnormality is present in the optical fiber cable only, and to control the selection circuit to select one of the first pixel information and the second pixel information depending on a presence of the transmission abnormality in the optical fiber cable; and
   an image processor configured to generate an image based on one of the first pixel information and the second pixel information selected based on the control of the control circuit.

2. The imaging apparatus according to claim 1, wherein the control circuit is configured to control the selection circuit to select and output to the image processor the pixel information received by the first receiver when the transmission abnormality is not present in the optical fiber cable, and to control the selection circuit to select and output to the image processor the pixel information received by the second receiver when the transmission abnormality is present in the optical fiber cable.

3. The imaging apparatus according to claim 1, further comprising:
   an electrical-to-optical converter circuit configured to stop an output of the pixel information to the optical fiber cable,
   wherein the control circuit is configured to control the electrical-to-optical converter circuit to stop the output of the pixel information output by the imaging sensor to the optical fiber cable when the transmission abnormality is present in the optical fiber cable.

4. The imaging apparatus according to claim 1, wherein
   the selection circuit implements a switching unit that switches a destination of outputting the pixel information output by the imaging sensor to one of the optical fiber cable and the electrical cable, and
   the control circuit is configured to control the switching unit to switch the destination of outputting the pixel information output by the imaging sensor to the optical fiber cable when the transmission abnormality is not present in the optical fiber cable, and the destination of outputting the pixel information output by the imaging sensor to the electrical cable when the transmission abnormality is present in the electrical cable.

5. The imaging apparatus according to claim 1, further comprising:
an extraction circuit configured to extract the portion of the pixel information output by the imaging sensor, and to output the portion of the pixel information to the electrical cable.

6. The imaging apparatus according to claim 1, wherein the imaging sensor comprises:
a plurality of pixels arranged in a matrix state and
a plurality of converters that are provided for respective lines in each of which a predetermined number of pixels are arranged, perform a signal conversion process with respect to the pixel information output by the imaging sensor, and then output the converted signal to the optical fiber cable, and
the pixel information output by a part of the plurality of converters is output to the optical fiber cable and also to the electrical cable via branching.

7. The imaging apparatus according to claim 1, further comprising:
a setting circuit capable of arbitrarily setting a pixel as a read-out target among the plurality of pixels in the imaging sensor,
wherein the imaging sensor is configured to output, as pixel information, the electrical signal after the photoelectric conversion from the pixel arbitrarily specified as the read-out target among the plurality of pixels for imaging.

8. The imaging apparatus according to claim 7, further comprising:
a reading circuit configured to read out pixel information by outputting pixel information from the pixel specified as the read-out target in the imaging sensor,
wherein the control circuit is configured to change the pixel as the read-out target set by the setting circuit.

9. The imaging apparatus according to claim 8, wherein the control circuit is configured to change the pixel as the read-out target set by the setting circuit to partial pixels extracted from all the pixels in the imaging sensor when the transmission abnormality is present in the optical fiber cable.

10. The imaging apparatus according to claim 8, wherein the selection circuit implements a switching unit that switches a destination of outputting the pixel information output by the imaging sensor to one of the optical fiber cable and the electrical cable, and
the control circuit is configured to control the switching unit to switch the destination of outputting the pixel information output by the imaging sensor to the optical fiber cable when the transmission abnormality is not present in the optical fiber cable, and the destination of outputting the pixel information output by the imaging sensor to the electrical cable when the transmission abnormality is present in the optical fiber cable.

11. The imaging apparatus according to claim 8, further comprising:
a connector configured to connect the imaging sensor and the electrical cable,
wherein the control circuit is configured to release the connection between the imaging sensor and the electrical cable when the transmission abnormality is not present in the optical fiber cable, and to connect the imaging sensor and the electrical cable when the transmission abnormality is present in the optical fiber cable.

12. The imaging apparatus according to claim 1, wherein the control circuit is configured to determine the transmission abnormality in the optical fiber cable based on a presence of the pixel information transmitted from the optical fiber cable.

13. The imaging apparatus according to claim 1, wherein an information volume which can be transmitted by the electrical cable is smaller than an information volume which can be transmitted by the optical fiber cable.

14. The imaging apparatus according to claim 1, wherein the optical fiber cable is configured to transmit, as the first pixel information, an optical signal obtained by converting the pixel information output by the imaging sensor, and
the electrical cable is configured to transmit, as the second pixel information, an electrical signal indicating the pixel information output by the imaging sensor.

* * * * *